United States Patent
Hugli et al.

(10) Patent No.: US 6,297,024 B1
(45) Date of Patent: *Oct. 2, 2001

(54) METHODS FOR ASSESSING COMPLEMENT ACTIVATION

(75) Inventors: Tony E. Hugli; Roland B. Stoughton, both of San Diego, CA (US)

(73) Assignees: Cell Activation, Inc., San Diego; The Scripps Research Institute, La Jolla, both of CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/245,829

(22) Filed: Feb. 5, 1999

Related U.S. Application Data

(63) Continuation-in-part of application No. 09/173,579, filed on Oct. 15, 1998.

(51) Int. Cl.[7] .............................. C12Q 1/37; C12Q 1/00
(52) U.S. Cl. ................................. 435/23; 435/24; 435/4
(58) Field of Search ................... 435/23, 24, 4

(56) References Cited

U.S. PATENT DOCUMENTS

| | | | |
|---|---|---|---|
| 3,884,896 | 5/1975 | Blomback et al. | 260/112.5 |
| 3,886,136 | 5/1975 | Claeson et al. | 260/112.5 |
| 4,016,042 | 4/1977 | Svendsen | 195/103.5 |
| 4,028,318 | 6/1977 | Aurell et al. | 260/112.5 R |
| 4,119,620 | 10/1978 | Nagatsu et al. | 260/112.5 R |
| 4,147,692 | 4/1979 | Nagatsu et al. | 260/112.5 R |
| 4,155,916 | 5/1979 | Smith et al. | 260/345.2 |
| 4,167,449 | 9/1979 | Gargiulo et al. | 435/16 |

(List continued on next page.)

FOREIGN PATENT DOCUMENTS

| | | |
|---|---|---|
| 0097440 | 6/1983 | (EP) . |
| 9500164 | 1/1995 | (WO) . |

OTHER PUBLICATIONS

Matsushita et al; Journal of Experimental Medicine, vol. 176, p 1497–1502, 1992.*

Björk et al., Microvascular Effects of Anaphylatoxins C3a and C5a, *Journal of Immunology* 134(2):1115–1119 (1985).

Carney et al., Site–specific mutations in the N–terminal region of human C5a that affect interactions of C5a with the neutrophil C5a receptor, *Protein Science* 2:1391–1399 (1993).

Cui et al., Primary structure and functional characterization of rat C5a: An anaphylatoxin with unusually high potency, *Protein Science* 3:1169–1177 (1994).

Daffern et al., C3a Is a Chemotaxin for Human Eosinophils but Not for Neutrophils. I. C3a Stimulation of Neutrophils Is Secondary to Eosinophil Activation, *J. Exp. Med.* 181:2119–2127 (1995).

(List continued on next page.)

*Primary Examiner*—Louise N. Leary
(74) *Attorney, Agent, or Firm*—Stephanie L. Seidman; Heller Ehrman White & McAuliffe LLP

(57) ABSTRACT

Methods for measuring in vivo activation of the lectin pathway by measuring mannan-binding serine protease activity (MASP) are provided. The methods are accomplished by C3a and C4a levels in in vitro activated EDTA plasma. In particular, the increase in C3a and/or C4a as a function of time is an indicator of the amount of activated MASP in EDTA plasma. Methods are also provided for measuring the alternate and classical pathways of complement activation, exclusive of the lectin pathway, and thereby disorders associated therewith. To perform such measurements, Futhan or other serine protease inhibitor is added to blood or plasma, containing a divalent metal ion chelator, and C3a and C4a are measured.

54 Claims, 3 Drawing Sheets

U.S. PATENT DOCUMENTS

| | | | |
|---|---|---|---|
| 4,191,808 | 3/1980 | Nagatsu et al. | 435/24 |
| 4,191,809 | 3/1980 | Nagatsu et al. | 435/24 |
| 4,207,232 | 6/1980 | Claeson | 435/23 |
| 4,210,497 | 7/1980 | Loquist et al. | 204/26 |
| 4,217,269 | 8/1980 | Cole | 260/112.5 |
| 4,221,706 | 9/1980 | Ali et al. | 260/11.5 R |
| 4,448,715 | 5/1984 | Ryan et al. | 260/112.5 R |
| 4,480,030 | 10/1984 | Svendsen | 435/13 |
| 4,563,305 | 1/1986 | Ryan et al. | 260/112.5 R |
| 4,568,636 | 2/1986 | Svendsen | 435/13 |
| 4,731,336 | 3/1988 | Satoh | 436/506 |
| 5,073,487 | 12/1991 | Lloyd | 435/23 |
| 5,100,899 | 3/1992 | Caine | 514/291 |
| 5,112,952 | 5/1992 | Mallia et al. | 530/387.1 |
| 5,116,735 | 5/1992 | Loesche | 435/34 |
| 5,164,495 | 11/1992 | Lunetta | 540/456 |
| 5,175,083 | 12/1992 | Moulds | 435/7.4 |
| 5,215,899 | 6/1993 | Dattagupta | 435/6 |
| 5,221,616 | 6/1993 | Kolb et al. | 435/18 |
| 5,223,403 | 6/1993 | Loesche et al. | 435/23 |
| 5,225,542 | 7/1993 | Cramer et al. | 530/396 |
| 5,472,939 | 12/1995 | Fearon et al. | 514/8 |
| 5,480,974 | 1/1996 | Morgan et al. | 530/387.9 |
| 5,612,033 | 3/1997 | Tsay et al. | 424/177.1 |
| 5,627,264 | 5/1997 | Fodor et al. | 530/350 |
| 5,679,546 | 10/1997 | Ko et al. | 435/69.2 |
| 5,778,895 | 7/1998 | Barnum et al. | 128/898 |
| 5,807,876 | 9/1998 | Armistead et al. | 514/374 |

OTHER PUBLICATIONS

Ember et al., Induction of Interleukin–8 Synthesis from Monocytes by Human C5a Anaphylatoxin, *American Journal of Pathology* 144(2):393–403 (1994).

Fischer et al., Regulation of B Cell Functions by C3a and C3a$^{desArg}$, *Journal of Immunology* pp. 4279–4286 (1997).

Fukuoka et al., Ligand Binding Sites on Guinea Pig C3aR: Point and Deletion Mutations in the Large Extracellular Loop and Vicinity, *Biochemical and Biophysical Research Communications* 263:357–360 (1999).

Hetland et al., Processing of C5a by human polymorphonuclear leukocytes, *Journal of Leukocyte Biology* 63:456–462 (1998).

Huey et al., Characterization of A C5a Receptor on Human Polymorphonuclear Leukocytes (PMN)[1], *Journal of Immunology* 135(3):2063–2068 (1985).

Morgan et al., Identification and Characterization of the Effector Region Within Human C5a Responsible for Stimulation of IL–6 Synthesis, *Journal of Immunology* 148(12):3937–3942 (1992).

Mousli et al., A Mechanism of Action for Anaphylatoxin C3a Stimulation of Mast Cells, *Journal of Immunology* 148(8):2456–2461 (1992).

Pfeifer et al., Plasma C3a and C4a levels in liver transplant recipients: a longitudinal study, *Immunopharmacology* 46(2):163–174 (2000).

Scholz et al., C5a–Mediated Release of Interleukin 6 by Human Monocytes, *Clinical Immunology and Immunopathology* 57:297–307 (1990).

Sun et al., Identification of ligand effector binding sites in transmembrane regions of the human G protein–coupled C3a receptor, *Protein Science* 8:2304–2311 (1999).

Abou–Ragheb et al., Plasma levels and mode of excretion of the anaphylatoxins C3a and C4a in renal disease, *J. Clin. Lab. Immunol.* 35:113–119 (1991).

Adams et al., Patterns of graft rejection following liver transplantation, *J. Hepatol.* 10:113–119 (1990).

Arlaud et al., A functional model of the human C1 complex, *Immunol Today* 8:106–111 (1987).

Baldwin et al., Complement in organ transplantation, *Transplantation* 59:797–808 (1995).

Bechtel et al., Assessment of soluable adhesion molecules (sICAM–1, sVCAM–1, sELAM–1) and complement cleavage products (sC4d, sC5b–9) in urine, *Transplantation* 58:905–911 (1994).

Berger (1998) Complement–mediated phagocytosis. The human complement system in health and disease.; Volanakis et al. eds., New York: Marcel Dekker, Inc., 12, p. 285–308.

Bodansky et al. "Peptide Synthesis", Table of Contents, Interscience Publishers (1966).

Bodansky et al., Active esters and resins in peptide synthesis, *Chem. Ind.* (*London*) 38:1597–98 (1966).

Bodansky et al. "The Practice of Peptide Synthesis," Springer–Verlag, Berlin (1984), p. 20.

Bodansky, Principles of Peptide Synthesis, Second, Revised Edition, Table of Contents, Springer–Verlag.

Bokisch et al., Anaphylatoxin inactivator of human plasma: its isolation and characterization as a carboxypeptidase, *J.Clin.Invest.* 49:2427–2436 (1970).

Bokisch et al., Isolation of fragment (C3a) of the third component of human complement containing anaphylatoxin and chemotactic activity and description of an anaphylatoxin inactivator of human serum, *J. Exp. Med.* 129(5):1109–30 (1969).

Borsos et al., Complement fixation on cell surfaces by 19S and 7S antibodies, *Science* 150(695):505–6 (1965).

Bottger et al., Complement and the regulation of humoral immune responses, *Immunology Today* 8:261–164 (1987).

Boulay, F. et al., Expression cloning of a receptor for C5a anaphylatoxin on differentiated HL–60 cells, 30:2993–2999 (1991).

Brauer et al., The contribution of therminal complement components to acute and hyperacute allograft rejection in the RAT[1,2], *Transplantation* 59:288–293 (1995).

Bronsther et al., Occurrence of cytomegalovirus hepatitis in liver transplant patients, *J. Med. Virol.* 24:423–434 (1988).

Buyon et al., Assessment of disease activity and impending flare in patients with systemic lupus erythematosus, *Arthritis Rheum.* 35:1028–1037 (1992).

Caporale et al., A fluorescent assay for the complement activation, *J. Immunol.* 15:1963–1965 (1981).

Chenoweth et al., The C5a receptor of neutrophils and macrophages, *Agents Actions Suppl* 12:252–273 (1983).

Chenoweth et al., Demonstration of specific C5a receptor on intact human polymorphonuclear leukocytes, Proceedings National Academy of Science 75:3943–3947 (1978).

Cornacoff et al., Primate erythrocyte–immune complex–clearing mechanism, *J. Clin. Invest.* 71:236–247 (1983).

Couser et al., The effects of soluble recombinant complement receptor 1 on complement–mediated experimental glomerulonephritis[1], *J Am Soc Nephrol.* 5:1888–1894 (1995).

Crosbie et al., Studies on stored blood, X. Complement, iso–agglutinins and agglutinogens, *Edinb. Med. J.* 49:766–772 (1942).

Dalmasso et al.The complement system in xenotransplantation, *Immunopharmacology* 24:149–160 (1992).

Davies, J. S. "Amino Acids, Peptides, and Proteins", vol. 29, The Royal Society of Chemistry: Cambridge, U.K. (1997).

Dyker, Amino acid derivatives by multicomponent reactions, *Angew. Chem., Int. Ed. Eng.* 36(16):1700–1702 (1997).

Easton, Free radical reactions in the synthesis of α–amino acids and derivatives, *Chem. Rev.* 97(1):53–82 (1997).

Ember et al., in *The Human Complement System in Health and Disease,* John E. Volanakis and Michael M. Frank eds. (Marcel Dekker) (1988).

Ember and Hugli, Complement factors and their receptors, *Immunopharmacology* 38:3–15 (1997).

Ember et al., Biologic activity of synthetic analogues of C5a anaphylatoxin, *J. of Immunology* 148(10):3165–3173 (1992).

Epstein et al., The collectins in innate immunity, *Curr Opin. Immunol.* 8:29–35 (1996).

Feucht et al., Capillary deposition of C4d complement fragment and early renal graft loss, *Kidney Int.* 43:1333–1338 (1993).

Fuecht et al., Vascular deposition of complement–split products in kidney allografts with cell–mediated rejection, *Clin. Exp. Immunol.* 86:464–470 (1991).

Frank, M. and Fries, L. Complement. In Paul, W. (ed.) *Fundamental Immunology,* Raven Press, pp. 679–701 (1989).

Fujii et al., New synthetic inhibitors of C1r, C1 esterase, thrombin, plasmin, kallikrein and trypsin, *Biochim. Biophys. Acta* 661:342–345 (1981).

Fujii et al., Defensins promote fusion and lysis of negatively charged membranes, *Protein Science* 2:1301–1312 (1993).

Gerard et al., The chemotactic receptor for human C5a anaphylatoxin, *Nature* 349:614–617 (1991).

Gewurz et al., Interactions of the complement system with endotoxic lipopolysaccharide: consumption of each of the six terminal complement components, *J. Exp. Med.* 128(5):1049–57 (1968).

Gisin, The preparation of merrifield resins through total esterification with cesium salts, *Helv. Chem. Acta* 56:1476 (1973).

Gordon et al., The antibody crossmatch in liver transplantation, *Surgery* 100:705–715 (1986).

Greene "Protective Groups in Organic Synthesis", second edition, Table of Contents, (Wiley–Interscience, 1991).

Hack et al., Elevated plasma levels of the anaphylatoxins C3A and C4a are associated with a fataloutcome in sepsis, *Am.J.Med.* 86:20–26 (1989).

Hecke et al., Circulating complement proteins in multiple trauma patients—correlation with injury severity, development of sepsis, and outcome, *Crit Care Med* 25(12):2015–2024 (1997).

Heideman et al., Anaphylatoxin generation in multisystem organ failure, *J.Trauma* 24 1038–1043 (1984).

Hitomi et al., Inhibition of various immunological reactions in vivo by a new synthetic complement inhibitor, *Int.Arch.Allergy Appl.Immunol.* 69:262–267 (1982).

Hitomi et al., Inhibitory effect of a new synthetic protease inhibitor (FUT–175) on the coagulation system, *Haemostasis* 15(3):164–168 (1985).

Hourcade et al., The regulators of complement activation (RCA) gene cluster, *Adv. Immunol.* 45:381–416 (1989).

Hugli, *Chemistry and Biology of Thrombin,* Lundblad et al., eds. p. 345–360, Ann Arbor Science, Ann Arbor (1977).

Hugli et al., 15th International Leucocyte Culture Conference, Asilomar, CA (Abstract) (1982).

Hugli et al., "Immunoassays: Clinical Laboratory Techniques for the 1980s," 443–460 (1980).

Hugli, Structure and function of C3a anaphylatoxin, *Curr. Top. Microbiol. Immunol.* 153:181–208 (1990).

Hugli (1984) Structure and Function of the Anaphylatoxins: Springer–Verlag, Heidelberg: Springer–Verlag, 7, p. 193–219.

Hugli et al., Purification and partial characterization of human and porcine C3a anaphylatoxin*, *J. Biol. Chem.* 250:1472–1478 (1975).

Hugli, Human anaphylatoxin (C3a) from the third component of complement, *J. Biol. Chem.* 250:8293–8301 (1975).

Hugli et al., Circular dichroism of C3a anaphylatoxin, *J. Biol. Chem.* 250:1479–1483 (1975).

Hugli et al. in Immune Biology, vol. 14 (Snyderman,R., Ed.), pp. 109–153, Plenum Publishing Company, New York (1984).

Humphrey et al., Chemical synthesis of natural product peptides: coupling methods for the incorporation of non-coded amino acids into peptides, *Chem. Rev.* 97(6):2243–2266 (1997).

Ikari et al., New synthetic inhibitor to the alternative complement pathway, *Immunology* 49:685–691 (1983).

Iwaki et al., Pharmacological studies of FUT–175, nafamostat mesilate. V. Effects on the pancreatic enzymes and experimental acute pancreatitis in rats, *J. Pharmacol.* 41:155–162 (1986).

Ji et al., Activation of the C4 and C2 components of complement by a proteinase in serum bactericidal factor, Ra reactive factor, *J. of Immunology* 150(2):571–578 (1993).

Ji et al., Ancient origin of the complement lectin pathway revealed by molecular cloning of mannan binding protein–associated serine protease from a urochordate, the Japanese ascidian, *Halocynthia roretzi, Immunology* 94:6340–6345 (1997).

Kaiser et al., Color test for detection of free terminal amino groups in the solid–phase synthesis of peptides, *Analyt. Biochem.* 34:595 (1970).

Kapoor A., Recent trends in the synthesis of linear peptides, *J. Pharm. Sci.* 59:1–27 (1970).

Kirschfink et al., Complement activation in renal allograft recipients, *Transplantation Proceedings* 24: 2556–2557 (1992).

Kistler et al., Cardiovascular activating factors from the pancrease, abstract, Biomedical Engineering Society (BMES) Conference, Atlanta, Georgia, Oct. 1999.

Kistler, Erik B., Humoral mechanisms of cellular activation in ischemic shock, A dissertation submitted in partial satisfaction of the requirements for the degree Doctor of Philosophy in Bioengineering, University of California, San Diego (1998).

Kolmer, Preserved citrated blood "banks" in relation to transfusion in the treatment of disease with special reference to the immunologic aspects, *Amer. J. Med. Sci.* 197:442–452 (1993).

Lerner, Richard A., Tapping the immunological repertoire to produce antibodies of predetermined specificity, 299:592–596 (1982).

Lipscombe et al., Distinct physicochemical characteristics of human mannose binding protein expressed by individuals of differing genotype, *Immunology* 85:660–667 (1995).

Lu et al., Binding of the pentamer/hexamer forms of mannan–binding protein to zymosan activates the proenzyme $C1r_2C1s_2$ complex, of the classical pathway of complement, without involvement of C1q, *J. of Immunology* 144(6):2287–2294 (1990).

Malhotra et al., Glycosylation changes of IgG associated with rheumatoid arthritis can activate complement via the mannose–binding protein, *Nature Medicine* 1(3):237–243 (1995).

Manez et al., Anomalous pattern of IgG antibody response to primary cytomegalovirus infection after solid organ retransplantation, *Transplantation* 59:1220–1223 (1995).

Marahiel et al., Modular peptide synthetases involved in nonribosomal peptide synthesis, *Chem. Rev.* 97(7):2651–2673 (1997).

Mason, Pharmacology of cyclosporine (sandimmune), VII. Pathophysiology and toxicology of cyclosporine in humans and animals, *Pharmacol. Rev.* 42:423–434 (1989).

Matsuda et al., The primary structure of L–1 light chain of chicken fast skeletal muscle myosin and its genetic implication, *FEBS Letters* 126(1):111–113 (1981).

Matsushita and Fujita, Cleavage of the third component of complement (C3) by mannose–binding protein–associated serine protease (MASP) with subsequent complement activation, *Immunobiol* 194:443–448 (1995).

Matsushita and Fujita, Chapter 8, MASP (MBP–Associated Serine Protease), Collections Innate Immunol., Ezekowitz et al. eds., pp. 165–182 (1996).

Matsushita et al., Complement–related serine proteases in tunicates and vertebrates, *Innate Immunity*, 29–35 (1998).

Maurer et al., Proteins and polypeptides as antigens, *Methods in Enzymology*, 70(A):49–70 (1980).

Mazzoni et al., Mechanisms and consequences of cell activation in the microcirculation, *Cardiovasc Res* 32(4):709–19 (1996).

McNearney et al., Membrane cofactor protein of complement is present on human fibroblast, epithelial and endothelial cells, *(1989) J. Clin. Invest.* 84:538–545.

Medof et al., Inhibition of complement activation on the surface of cells after incorporation of decay–accelerating factor (DAF) into their membranes, *J. Exp. Med.* 160:1558–1578 (1984).

Medof et al., Control of the function of substrate–bound C4b–C3b by the complement receptor CR1, *J. Exp. Med.* 159:1669–1685 (1984).

Meuer et al., Comparative study on biological activities of various anaphylatoxins (C4a, C3a, C5a), investigations on their ability to induce platelet secretion[1], *Inflammation* 5:263–273 (1981).

Mitsuoka et al., Inhibition of intestinal proteases decreases cellular activation in SAO shock, abstract, Biomedical Engineering Society (BMES) Conference, Atlanta, Georgia, Oct. 1999.

Moon et al., Complete primary structure of human C4a anaphylatoxin, *J. Biol. Chem.* 256(16):8685–92 (1981).

Mor et al., Late–onset acute rejection in orthotopic liver transplantation—associated risk factors and outcome, *Transplantation* 54:821–824 (1992).

Morgan, Complement fragment C5a and immunoregulation[1], *Complement Today* 1:56–75 (1993).

Morgan et al., Anti–C5a receptor antibodies, *J. of Immunology* 151(1):377–388 (1993).

Morgan et al., Anaphylatoxin–mediated regulation of the immune response, *J.Immunol.* 130: 1257–1261 (1983).

Morgan et al., Anaphylatoxin–mediated regulation of the immune response, *J.Exp.Med.* 155:1412–1426 (1982).

Moxley et al., Elevated plasma C3 anaphylatoxin levels in rheumatoid arthritis patients, *Arthritis & Rheumatism* 30:1097–1104 (1987).

Müller–Eberhard, Complement[1,2], *Ann Rev Biochem* 38:389–414 (1969).

Müller–Eberhard, Molecular organization and function of the complement system, *Ann.Rev.Biochem.* 57:321–347 (1988).

Nicholson–Weller et al., Isolation of a human erythrocyte membrane glycoprotein with decay–accelerating activity of C3 convertases of the complaint system[1], *J. Immunol.* 129:184–189 (1982).

Ochs et al., The role of complement in the induction of antibody responses, *Clin. Exp. Immunol.* 53:208–216 (1983).

Ogata et al., Substrate specificities of the protease of mouse serum Ra–reactive factor, *J. of Immunology* 2351–2357 (1995).

Ohta et al., The mechanism of carbohydrate–mediated complement activation by the serum mannan–binding protein, *J. of Biolog. Chemistry* 285 (4):1960–1984 (1990).

Oppermann et al., Probing the human receptor for C5a anaphylatoxin (C5aR) with anti–peptide antibodies, *Immunobiology* 186(1–2):58 (1992).

Otterness et al., Complement inhibition by amidines and guanidines—in vivo and in vitro results, *Biochem Pharmacol* 27:1873–1878 (1978).

Pfeifer et al., Possible mechanism for in vitro complement activation in blood and plasma samples: Futhan/EDTA controls in vitro complement activation, *Clin. Chem.* 45:1190–9 (1999).

Pfeifer et al., Plasma C3a and C4a levels in liver transplant recipients: a longitudinal study, abstract, XVII International Complement Workshop, Rhodes, Greece, Oct. 11–16, 1998.

Pfeiffer et al., Complement activation of EDTA blood/plasma samples may be caused by coagulation proteases, *Techniques in Protein Chemistry VIII*, Marshak, Ed., pp. 363–369, Academic Press, San Diego (1997).

Prizont et al., Antacids and drug trials for duodenal ulcer, *Lancet* 1:896–897 (1989).

Reich et al., Complement preservation in citrated human blood, *Transfusion* 10:14–16 (1970).

Reid (1998) C1q and mannose–binding lectin. The human complement system in health and disease, Valanakis et al. eds., New York: Marcel Dekker, Inc., 3, p. 33–48.

Reid et al., Complement component CI and the collectins: parallels between routes of acquired and innate immunity, *Immunology Today* 19(2):56–59 (1998).

Reid et al., The proteolytic activation systems of complement, *Annu Rev Biochem* 50:433–64 (1981).

Ronholm et al., Complement system activation during orthopedic liver transplantation in man, *Transplantation* 57:1594–1597 (1994).

Sato et al., Molecular characterization of a novel serine protease involved in activation of the complement system by mannose–binding protein, *International Immunology* 6(4):665–669 (1994).

Satoh et al., The Journal of the European Society for Artificial Organs, Proceedings of the XIII Annual Meeting 4(2): (1986).

Sauerbrei et al., Enzymatic synthesis of peptide conjugates—tool for the study of biological signal transduction, *Top. Curr. Chem.* 186:65–86 (1997).

Scherer et al., A novel serum protein similar to C1q, produced exclusively in adipocytes, *J. of Biological Chemistry* 270(45):26746–26749 (1995).

Schmid–Schonbein et al., Mechanisms of leukocyte activation in the circulation, *Atherosclerosis* 131:S23–5 (1997).

Schmid–Schonbein, The damaging potential of leukocyte activation of the microcirculation, *Angiology* 44(1):45–56 (1993).

Schmid–Schonbein et al., Perspectives of leukocyte activation in the microcirculation, *Biorheology* 27(6):859–69 (1990).

Schroeder et al., Competitive protein binding assay for biotin monitored by chemiluminescence, *Anal. Chem.* 48:1933 (1976).

Seya et al., Preferential inactivation of the C5 convertase of the alternative complement pathway by factor 1 and membrane cofactor protein (MCP)*, *Mol. Immunol.* 28:1137–1147 (1991).

Seya et al., Purification and characterization of a membrane protein (gp45–70) that is a cofactor for cleavage of C3b and C4b, *Exp. Med.* 163:837–855 (1986).

Seya et al., Functional properties of membrane cofactor protein of complement, *Biochem. J.* 264:581–588 (1989).

Sheriff et al., Human mannose–binding protein carbohydrate recognition domain trimerizes through a triple $\alpha$–helical coiled–coil, *Structural Biology* 1(11):789–794 (1994).

Sim et al., Kinetics of reaction of human C1–inhibitor with the human complement system proteases C1r and C1s, *Biochem Biophys Acta* 612:433–449 (1980).

Simpson et al., A stable chemiluminescent–labelled antibody for immunological assays, *Nature* 279:646 (1979).

Snover et al., Liver allograft rejection, *Am. J. Surg. Pathol.* 11:1–10 (1987).

Sonntag et al., Anaphylatoxins in fresh–frozen plasma, *Transfusion* 37:798–799 (1997).

Spatola (1983) pp. 267–357 in *Chemistry and Biochemistry of Amino Acids, Peptides, and Proteins*, Weistein, Ed. vol. 7, Marcel Dekker, New York.

Stevens et al., Effects of anti–C5a antibodies on the adult respiratory distress syndrome in septic primates, *J.Clin.Invest.* 77:1812–1816 (1986).

Stewart et al. ("Solid Phase Peptide Synthesis," 2nd Edition, Pierce Chemical Co., Rockford, Illinois (1984), Chapter 2, pp. 27–64.

Stove et al., Circulating complement proteins in patients with sepsis or systemic inflammatory response syndrome, *Clin Diag Lab Immunol* 3:175–183 (1996).

Suankratay et al., Requirement for the alternative pathway as well as C4 and C2 in complement–dependent hemolysis via the lectin pathway, *J. of Immunology* 3006–3013 (1998).

Takayama et al., A 100kDa protein in the C4–activating component of Ra–reactive factor is a new serine protese having module organization similar to C1r and C1s[1], *J. Immunol.* 152:2308–2316 (1994).

Tan et al., Improvements on the purification of mannan–binding lectin and demonstration of its $Ca^{2+}$–independent association with a C1s–like serine protease, *Biochem. J.* 319:329–332 (1996).

Terai et al., Human serum mannose–binding lectin (MBL)–associated serine protease–1 (MASP–1): determination of levels in body fluids and identification of two forms in serum, *Clin. Exp. Immunol.* 110:317–323 (1997).

Thiel et al., The concentration of the C–type lectin, mannan–binding protein, in human plasma increases during an acute response, *Clin. Exp. Immunol.* 90:31–35 (1992).

Thiel et al., A second serine protease associated with mannan–binding lectin that activates complement, *Nature* 386:506–510 (1997).

Vallota et al., Formation of C3a and C5a anaphylatoxins in whole human serum after inhibition of the anaphylatoxin inactivator, *J. Exp. Med.* 137(5):1109–23 (1973).

van Son et al., Pulmonary dysfunction is common during a cytomegalovirus infection after renal transplantation even in asymptomatic patients, *Am. Rev. Respir. Dis.* 136:580–585 (1987).

Volanakis and Arlaud, Complement enzymes, Chapter 4, In: The human complement system in health and disease, Volanakis JE and Frank MM, eds., New York Marcel Dekker, Inc., 4:49–81 (1998).

von Döhren et al., Multifunctional peptide synthetases, *Chem. Rev.* 97(7): 2675–2705 (1997).

Wagner and Hugli, Radioimmunoassay for anaphylatoxins: a sensitive method for determining complement activation products in biological fluids, *Analytical Biochemistry* 136:75–88 (1984).

Wahlin et al., C3 receptors on human lymphocyte subsets and recruitment of ADCC effector cells by C3 fragments[1], *J. Immunol.* 130:2831–2836 (1983).

Wang et al., Amelioration of lupus–like autoimmune disease in NZB/W $F_1$ mice after treatment with a blocking monoclonal antibody specific for complement component C5, *Proc. Natl. Acad. Sci. U.S.A.* 90:8563–8568 (1996).

Wang et al., Anti–C5 monoclonal antibody therapy prevents collagen–induced arthritis and ameliorates established disease, *Proc. Natl. Acad. Sci. U.S.A.* 92:8955–8959 (1995).

Watkins et al., Nafamostate to stabilise plasma samples taken for complement measurements, *Lancet* 1(8643):896–7 (1989).

Watkins J., Investigation of allergic and hypersensitivity reactions to anaesthetic agents, *Br. J. Anaesth* 59(1):104–11 (1987).

Watson et al., *Molecular Biology of the Gene*, 4th Edition, 1987, The Bejacmin/Cummings Pub. Co., p.224.

Williams in "Advances in Asymmetric Synthesis", vol. 1, Hassner, A., ed., JAI: Greenwich, CT (1995).

Wuepper et al., Cutaneous responses to human C3 anaphylatoxin in man, *Clin Exp Immunol* 11(1):13–20 (1972).

Yokota et al., Oligomeric structures required for complement activation of serum mannan–binding proteins, *J. Biochem.* 117:414–419 (1995).

Zilow et al., Complement activation and the prognostic value of C3a in patients at risk of adult respiratory distress syndrome, *Clin.Exp.Immunol.* 79:151–157 (1990).

Partrick, et al., "Reduced PAF–Acetylhydrolase activity is associated with postinjury multiple organ failure", *Shock* 7(3):170–174 (1997).

Sato et al., Substances Reactive With Mannose–Binding Protein (MBP) In Sera Of Patients With Rheumatoid Arthritis, *Fukishima J. Med. Sci.*, 43(2):99–111 (1997).

* cited by examiner

MASP Enzyme Test Greatly Enhances
Proposed Liver Transplant Immuno Assay Panel

| Type of Test | Test for | Hypothetical Outcome | | | | | |
|---|---|---|---|---|---|---|---|
| Immunosuppressant Titration | CsA* | (Used for Dose Control–but not held in high esteem) | | | | | |
| Toxicity | Bilirubin | High | Low | High | High | Low | Low |
| Function | Liver Enzymes | High | High | High | Low | Low | Low |
| Infection/ Immune Response/ Tissue Injury | Clinical Signs (temp) | High | High | High | Low | High | Low |
| | MASP | High | High | High | High | Low | Low |
| Diagnosis | | Acute Rejection | | Viral Infection /Immune Injury | Incipient Rejection | Bacterial Infection | OK |

*FK506

Advantages:
Detect and monitor viral infections and distinguish from bacterial
Early detection of organ rejection
Reduce biopsy rate and associated cost and morbidity (~1-2% hospitalizations from complications)

FIG. 3

METHODS FOR ASSESSING COMPLEMENT ACTIVATION

RELATED APPLICATIONS

This application is a continuation-in-part of co-pending U.S. application Ser. No. 09/173,579, filed Oct. 15, 1998, to Tony Hugli and Roland Stoughton, entitled "METHODS FOR ASSESSING COMPLEMENT ACTIVATION." The subject matter of the co-pending application is incorporated in its entirety.

Some of the work described herein was supported by National Institutes of Health Grant 5T32HL07195-20 and by National Institutes of Health Grant RO1-DE-10992 (TEH) from the US Public Health Service. The government, thus, may have some rights in the subject matter disclosed herein.

FIELD OF THE INVENTION

The present invention relates to methods for assessing in vivo mannan-binding protein-associated serine protease (MASP-1 and MASP-2) activity and for monitoring in vitro and in vivo complement-activation (C-activation).

BACKGROUND OF THE INVENTION

The complement (C) system of humans and other mammals involves more than 20 components that participate in an orderly sequence of reactions resulting in complement activation. The blood complement system has a wide array of functions associated with a broad spectrum of host defense mechanisms including anti-microbial and anti-viral actions (Muller-Eberhard (1988) *Annu.Rev.Biochem.* 57:321–347; Rother et al. (1984) in Contemporary Topics in Immunology, Vol. 14 (Snyderman, R., Ed.), pp. 109–153, Plenum Publishing Company, New York). Products derived from the activation of C components include non-self recognition molecules C3b, C4b and C5b, as well as the anaphylatoxins C3a, C4a and C5a that influence a variety of cellular immune responses (Hugli et al (1982) 15th International Leucocyte Culture Conference, Asilomar, CA (Abstract); Fujii et al. (1993) *Protein Science* 2:1301–1312; Morgan et al. (1982) *J.Exp.Med.* 155:1412–1426; Morgan (1993) *Complement Today* 1:56–75; Morgan et al. (1983) *J.Immunol.* 130:1257–1261). These anaphylatoxins also act as pro-inflammatory agents (Chenoweth et al. (1983) *Agents Actions* 12:252–273; Hugli et a. (1978) in Advances in Immunology, Dixon et a., Eds., pp. 1–53, Academic Press, New York). The role of C in the C system also has a role in immuno-pathogenesis of a number of disorders, including autoimmune diseases such as rheumatoid arthritis (see, e.g., Wang et al. (1995) *Proc. Natl. Acad. Sci. U.S.A.* 92:8955–8959; Moxley et al. (1987) *Arthritis & Rheumatism* 30:1097–1104), lupus erythematosus (Wang et al. (1996) *Proc. Natl. Acad. Sci. U.S.A.* 90:8563–8568; and Buyon et al. (1992) *Arthritis Rheum.* 35:1028–1037) and acute glomerulonephritis (Couser et al. (1995) *J Am Soc Nephrol.* 5:1888–1894). Other pathologies that involve activation of the C system include sepsis (see, e.g., Stove et al. (1996) *Clin Diag Lab Immunol* 3:175–183; Hack et al. (1989) *Am.J.Med.* 86:20–26), respiratory distress syndrome (see, e.g., Zilow et al. (1990) *Clin.Exp.Immunol.* 79:151–157; and Stevens et al (1986) *J.Clin.Invest.* 77:1812–1816) and multiorgan failure (see, e.g., Hecke et al. (1997) *Shock* 7:74; and Heideman et al. (1984) *J.Trauma* 241038–1043). Interest in such pathologies as well as interest in C-activation associated with transplanted organ rejection (see, e.g., Dalmasso et al. (1992) *Immunopharmacology* 24:149–160; Kirschfink et al. (1992) *Transplantation Proceedings* 24: 2556–2557) reveals a need for a reliable and accurate assay system for monitoring in vivo C-activation in patient populations.

The complement system is made up of an array of enzymes and non-enzymatic proteins and receptors. The enzymes include a group of seven serine proteases: factor D, C1r, C1s, MASP, factor B, C2 and factor I. Complement activation occurs by one of three primary modes known as the "classical" pathway, the "alternative" pathway and the lectin pathway (see FIGS. 1a and 1b; see, also, e.g., Ember et al. (1997) *Immunopharmacology* 38:3–15).

These pathways are distinguished by the processes that initiate complement activation. The classical pathway (see FIG. 1a) is initiated by antibody-antigen complexes or aggregated forms of immunoglobulins; the alternative pathway is initiated by several ways, including spontaneous cleavage of a thioester, by certain structures on microbial and cell surfaces, such as amino groups, hydroxyl groups, and by water, and the lectin pathway, which is an antibody-independent pathway that is initiated by the binding of mannan-binding lectin (MBL, also designated mannan-binding protein) to carbohydrates (see, e.g., Thiel et al. (1997) *Nature* 386:506–510).

Complement Pathways

Classical

The classical pathway is initiated by the binding of the first complement component (C1) to immune complexes through C1q, a subcomponent involved in binding to antibody. The c1 complex is composed of C1q and two homologous serine proteases, C1r and C1s (1:2:2 molar ratio). After binding to the immune complexes C1q undergoes a conformational change resulting in the conversions of C1r and C1s to their activated forms. Activated C1s cleaves C4 and C2 to generate a complex of their fragments C4b2a, which in turn cleaves C3 into C3a and C3b. C3b binds to immune complexes.

Alternative

The alternative pathway is activated by microbes without involvement of antibody. C3b molecules generated from C3 by interaction of C3 with two serine proteases, factors B and D, are deposited on the microbial surface where activation of C3 is amplified. C3b produced by activation of either pathway acts as a central molecule in the subsequent formation of membrane attack complexes that can lyse microbes and also as an opsonin.

Lectin

Another of complement activation, called the lectin pathway (see, Reid (1998) in The human complement system in health and disease; Volanakis et al., Eds., pp. 33–48, Marcel Dekker, Inc., New York) exists. This pathway involves a mannan-binding protein (MBP), also designated mannose-binding lectin (MBL), that is identical to the bactericidal Ra-reactive factor that binds to the Ra polysaccharides on various strains of bacteria (Ji et al. (1993) *J. Immunol.* 150:571–578). MBP is a multi-chain, multi-subunit protein that functions in a similar manner to the C1q component of the classical pathway. There are two proteinases associated with MBL called mannose-binding protein associate serine proteinases or MASP-1 and MASP-2 (see, e.g., Thiel et al. (1997) *Nature* 386:506–510; see, also Takayama et al. (1994) *J. Immunol.* 152:2308–2316). The MBL-MASP-1-MASP-2 complex is activated via MBL binding to neutral sugars resulting in activated MASP-2 enzyme which then cleaves component C4, and possibly the components C2 and C3, to initiate the classical complement pathway.

The collectin MBP, with its associated proteases, has the ability to activate complement and to act as an opsonin (a serum substance, that coats particulates such as viruses to promote phagocytosis). MBP-mediated complement activation is triggered by viruses and other pathogens and stimuli on which neutral sugar residues are exposed (see, Reid et al. (1998) *Immunology Today* 19:56–59). In particular, MBP binds to carbohydrates on microbial and viral surfaces. This pathway differs from the classical and alternative pathways of complement activation. Complement activation via this pathway is mediated by an MBP complex. MBP is associated with serine proteases designated MBP-associated serine proteases (MASP-1 and MASP-2). The complex has C4- and C3-activating capacities upon binding to mannan. The complex contains two serine proteases MASP-1 and MASP-2 linked by a disulfide bond. In this form, MASP is capable of cleaving C4 and C3.

The MBP-MASP-mediated complement cascade accompanied by C4 and C3 activation is distinct from the classical and alternative pathways and is designated the lectin pathway (see, e.g., FIG. 1).

MBL is structurally related to the complement C1 subcomponent C1q and appears to activate the complement system through an associated serine proteases MASP-1 (see, e.g., Sato et al. (1994) *International Immunol.* 6:665–669) and MASP-2 (see, e.g., Thiel et al. (1997) *Nature* 386:506–510). MBL binds to specific carbohydrate structures on the surface of microorganisms, including bacteria, yeast, parasitic protozoans and viruses, and exhibits antibacterial activity through lytic complement components or by promoting phagocytosis.

Relationships Among the Pathways

These pathways are important components of the immune response to bacterial and viral infection. The classical pathway attenuates the humoral response and is initiated by antibody antigen complexes. The alternative pathway represents the first line of defense and is activated by a variety of macromolecules, including bacterial lipopolysaccharide, teichoic acids and immune aggregates. Activation of the cascades results in production of complexes involved in proteolysis or cell lysis and peptides involved in opsonization, anaphylaxis and chemotaxis. The following table sets forth biologically active products of complement activation:

| Product | Activity |
| --- | --- |
| C3 | Release of neutrophils from bone marrow |
| C3a | Anaphylatoxin and eosinophil chemotoxin |
| C3b | Mediates phagocytosis of cells via specific lymphocyte receptors, opsonin, co-factor of convertases |
| C4a | Weak anaphylatoxin, spasmogen |
| C4b | Virus neutralization, opsonin, co-factor of convertases |
| C5a | Anaphylatoxin, chemotactic for leukocytes and monocytes |
| C5b-9 | Terminal complement complex (TCC) involved in cell lysis |

Regulatory proteins of the complement system have been identified. Their primary functions are to regulate the activity of C3/C5 convertases for prevention of excessive complement activation and autolytic destruction of host tissues. These complement regulators are either soluble plasma proteins or integral membrane proteins expressed on a variety of cell types. The former include C4b binding protein (C4bp) and Factor H. The latter include the C3b/C4b receptor (Complement receptor 1, CR1, CD35), membrane cofactor protein (MCP, CD46), and decay accelerating factor (DAF, CD55). These proteins possess many structural similarities. Each is composed of multiple short consensus repeats (SCRs) of approximately 60 amino acids in length having conserved cysteine, glycine and proline residues. The genes encoding these proteins have been localized to chromosome 1 and are collectively known as the regulators of complement activation (RCA) gene cluster (Hourcade et al. (1989) *Adv. Immunol.* 45:381). In addition to its role in regulating complement activation, erythrocyte CR1 also functions as a receptor for circulating immune complexes to promote their clearance from plasma (Cornacoff et al. (1983) *J. Clin. Invest.* 71:236).

MCP and DAF proteins prevent autolytic destruction of host tissues by complement activation. MCP (see, Seya et al. (1986) *Exp. Med.* 163:837; Seya et al. (1989) *Biochem. J.* 264:581) binds to C3b and C4b and possesses Factor I cofactor activity. MCP irreversibly inactivates C3b and C4b by proteolytic cleavage to C3bi and C4bi. MCP preferentially binds to C3b, thus making it a more potent inactivator of alternative pathway convertases (Seya et al. (1991) *Mol. Immunol.* 28:1137).

DAF (see, Nicholson-Weller et al. (1982) *J. Immunol.* 129:184) Medofet et al. (1984) *J. Exp. Med.* 160:1558) binds to C3b and C4b and dissociates these molecules from the C3 convertase, thus promoting the decay (inactivation) of the convertase. DAF inactivates alternative and classical convertases.

MCP and DAF are composed of only four SCRs, making them the smallest of the complement regulatory proteins. MCP does not possess decay accelerating activity and DAF does not possess cofactor activity. Both proteins are expressed in a variety of cell types, including endothelial cells, fibroblasts, lymphocytes, granulocytes and monocytes (Hourcade et al. (1989) *Adv. Immunol.* 45:381; McNearny et al. (1989) *J. Clin. Invest.* 84:538). MCP and DAF are considered to function, via different complementary mechanisms, as intrinsic inhibitors of complement activation to prevent complement-mediated autolysis of host cells.

Although the pathways converge to produce C5-9, they are distinguishable. In the alternative pathway, the cleavage of the C3 component of complement into its C3a and C3b fragments is one of the significant events signalling activation of the alternate complement cascade. Following the conversion of C3a, a C5 convertase enzyme complex is formed. This enzyme cleaves the C5 component to yield the fragments C5a and C5b (see, e.g., FIGS 1*a* and 1*b*). Complement activation by the classical pathway mechanism is uniquely characterized by the fact that this route leads to the conversion of the C4 to its fragments C4a and C4b.

The physicochemical and physiological properties of each of the cleavage products C3a, C4a and C5a, termed anaphylatoxins, are known. Each is a potent bioactive polypeptide and plays a key role as a mediator of acute inflammatory processes. Among the three anaphylatoxins, C5a is characterized by its ability to interact with white blood cells. C3a and C4a are rendered spasmogenically inactive in vivo by conversion of the respective des arginine derivatives (C3a des Arg or C3ai C4ai des Arg or C4ai) by a serum carboxypeptidase. Human C5a is converted to C5a des Arg by this serum carboxypeptidase.

Conversion of the human complement components C3 and C5 to yield their respective anaphylatoxin products has been implicated in certain naturally occurring pathologic states including: autoimmune disorders such as systemic lupus erythematosus, rheumatoid arthritis, malignancy, myocardial infarction, Purtscher's retinopathy, sepsis and adult respiratory distress syndrome. In addition, increased circulating levels of C3a and C5a have been detected in certain conditions associated with iatrogenic complement activation such as: cardiopulmonary bypass surgery, renal dialysis, and nylon fiber leukaphoresis. Elevated levels of C4a anaphylatoxin is associated with the autoimmune disorders mentioned above.

Regardless of which initiation pathway is used, the end result is the formation of activated fragments of complement proteins (e.g. C3a, C4a, and C5a anaphylatoxins and C5b-9 membrane attack complexes). These fragments mediate several functions including leukocyte chemotaxis, activation of macrophages, vascular permeability and cellular lysis (Frank, M. and Fries, L. Complement. In Paul, W. (ed.) Fundamental Immunology, Raven Press, 1989).

Therefore, the ability to quantitatively measure the circulating levels of these anaphylatoxins or their des-Arg derivatives would be of utility in diagnosing a variety of important pathological conditions. Additionally, the ability to measure levels of C4a and C4a des Arg permits determination of the pathway by which complement activation occurs, thereby permitting a determination of the precise mechanism of complement activation and also whether natural immunological defense mechanisms are functional.

Various methods for measuring C3a, C4a, C5a and their des arg derivatives are known (see, Hugli et al. (1980) in "Immunoassays: Clinical Laboratory Techniques for the 1980s," 443–460, Alan R. Liss, Inc., New York, N.Y. and Wagner et al. (1984) Analyt. Biochem. 136:75–88) for an RIA method. Commercial kits are also available from, for example, Amersham and are well known (see, e.g., U.S. Pat. No. 4,731,336)

Neither of the major C-activation pathways (i.e. the classical and alternative pathways), however, can function in the presence of the metal chelator EDTA (see, e.g., Muller-Eberhard (1969) Ann Rev Biochem 38:389–414). Drawn EDTA blood samples exhibit extensive in vitro C-activation, complicating the development of accurate assay systems and impeding the development of a reliable complement assay for research and clinical applications.

In vitro C Activation

Since the discovery of the C system, "spontaneous" loss of C activity in serum or plasma samples stored in vitro has remained a problem. Early definitions of the complement system invariably included a statement about the lability of C present in serum or plasma stored at 4° C. or at room temperature (22° C.) (see, e.g., Reich et al. (1970) Transfusion 10:14–16; Kolmer (1939) Amer. J. Med. Sci. 197:442–452; Crosbie et al. (1942) Edinb. Med. J. 49:766–772). The storage of serum and plasma samples under conditions allowing for the retention of full C activity has always been a problem for basic research and clinical laboratories. This has been solved in part by addition of EDTA to blood, serum and plasma.

The utility of complement (C) assays has been minimized by an inability to stabilize C components in blood or plasma samples and prevent in vitro activation. It is known that C3a and C4a levels in EDTA plasma from certain patients (i.e. autoimmune, trauma, sepsis and organ transplant patients) are greatly elevated but unreliable due to in vitro activation. Even EDTA plasma from normal individuals continues to undergo low level C-activation, particularly cleavage of component C4 to C4a and C4b. EDTA blood samples require immediate processing and analysis of the plasma to avoid further time-dependent C-activation. In designing a routine diagnostic C assay for the clinical laboratory, sample stabilization becomes a key issue. Consequently, understanding the mechanism of in vitro C-activation is as important as developing a method to control it.

Therefore, it is an object herein to provide a methods for controlling in vitro C-activation and, thus, accurately assess in vivo C-activation. It is also an object herein to provide a means to measure in vivo levels of activated MASP enzymes. It is also an object herein to provide ways to assess pathologies associated with activation of the lectin pathway.

SUMMARY OF THE INVENTION

Methods for assessing in vivo activation of complement pathways and the use thereof for diagnosis are provided. In particular, methods for measuring in vivo activation of the lectin pathway are provided. Also provided are methods for accurately assessing in vivo activation of the alternate and classical pathways.

In vivo activation of the lectin pathway is effected by measuring in vitro MASP activity. It is shown herein, that MASP enzyme(s) is responsible for the in vitro complement activation observed in plasma that contains a chelator, particularly a divalent ion chelator, such as EDTA. As shown herein MASP, particularly MASP-2, activity can only be measured after exposure of the MBL-MASP complexes to a metal chelator, such as in the presence of EDTA in EDTA plasma. Under these conditions, the activated MASP enzyme is able to cleave substrates. The observed increases in, for example, C4a concentration in EDTA plasma that are observed over time, is a reflection of the amount of activated MASP enzyme in the complex when the blood was drawn. Therefore, in order to measure such activity, and to thereby monitor diseases for which MASP activity, particularly MASP-2 activity, is an indicator, C3a and C4a increases over time in EDTA plasma are measured. Exposure to EDTA or other agent that removes metal ions, particular calcium ions, allows for measurement of the activated MASP that was in the complex. Removal of calcium inhibits activity of other complement components in the plasma, but does not inhibit activity of activated MASP.

Activated MASP is assessed by measuring the increase in C3a and C4a in plasma, containing a metal chelator, over time or by measuring the amount at a selected time point, while the amount is increasing linearly with time, compared to a standard or a control. The increase in C3a and C4a in the plasma, containing the chelator, or relative amount above a control or standard in the plasma, containing the chelator, is an indicator of MASP activating factors, such as pathogens, including viruses, particularly coated viruses, and parasites, and tissue injury to which the plasma was exposed in vivo.

It is also shown herein, that the kinetics of MASP activity or the amount of MASP activity, particularly MASP-2, but also MASP-1, is a useful parameter for assessing immune response initiated exposure to neutral sugars, and is particularly useful for assessing parasitic infections, such as malaria, and viral infections, such as cytomegalovirus (CMV), hepatitis (B and C) and HIV, other infections, tissue injury and other immune responses that result in exposure of MBL to neutral sugars, the activating agents for MASP activity in mammals, particularly, humans.

Thus, monitoring MASP, particularly MASP-2, activity in plasma, containing a metal chelator, such as EDTA or citrate, provides an indicator of any event that exposed neutral sugars to the complex in vivo, such as viral and parasitic diseases and tissue and organ injury, including transplanted organs, which resulted in activating MASP in the MASP-MBL complex.

As shown herein, MASP activity can be used to assess these conditions and parameters in man and in animals, particularly test animals. MASP activity is measured by determining C3a and C4a activity in plasma containing a metal chelator, particularly a divalent metal chelator, such as EDTA or citrate, particularly as a function of time. Any methods known to those of skill in this art for measuring C3a and C4a can be used.

Methods for detecting and monitoring acute organ transplant rejection, chronic rejection, incipient rejection, viral/parasitic infection and bacterial infections are provided. Methods for detecting and monitoring tissue injury and inflammatory responses are also provided. In practicing the methods, MASP activity is measured and correlated with these various outcomes.

Also provided is a panel of tests for organ transplants, particularly liver transplants. One such panel of tests, which includes the MASP test provided herein, is depicted in FIG. 3.

Methods for assessing the efficacy of therapeutic treatments for infectious agents, tissue injury and inflammatory responses in which C activation is mediated or initiated by exposure of neutral sugars, such as on cell surfaces of injured tissue, viruses and parasites are provided. Methods for monitoring toxicity or injury from therapeutic treatments or test agents are also provided. Similarly, such methods in which the alternative or classical pathway is implicated are also provided.

Longitudinal measurement of plasma C4a levels in particular reflects the status of humoral immune responses to allografts, to certain viruses and parasites and tissue injury. Measurement of C3a and C4a levels thus are tools for early detection of various types of infections, as distinguished from their elevation during acute allograft rejection episodes. The information provided by comparing historic with current levels of these plasma complement products from individual patients provides a unique parameter for assessing effectiveness of immuno-suppressive therapy and offers a clear signal of epi-phenomena such as viral infections not readily detected by conventional blood monitoring of organ function.

Also provided are methods to measure the alternative and classical pathways of C-activation and thereby conditions, diseases and disorders associated therewith. To perform such measurements, Futhan or other MASP inhibitor is added to EDTA blood, and C3a and C4a levels are measured. Since as shown herein MASP activity in vitro that results upon removal of calcium from the medium is responsible for in vitro increases in C3a and C4a, blocking MASP activity will inhibit in vitro activation. Inhibitors of MASP activity include serine proteases, particularly Futhan. Futhan blocks the MASP activity in the blood or plasma. Measurement of C3a and C4a reflects circulating levels generated by primarily by alternative and classical pathways because complexed MASP, whether activated or not, does not generate conversion of these factors in vivo (i.e., in a fluid phase, such as blood).

Reliable estimates of the circulating levels of C3a, C4a and C5a can be used as an index of in vivo C-activation only if in vitro activation is totally eliminated. Because the mechanism for this activation is shown herein to be MASP activity, means for inhibiting in vitro C activation by inhibiting MASP activity have been developed. By inhibiting MASP activity, it is possible to perform in vivo (i.e. circulating) measurements of intact components as well as C3a and C4a levels by avoiding the artifact of in vitro C-activation.

As described above, the methods provided herein are based on the discovery that in circulation, the complex of MASP-1, MASP-2 and MPL can be in an activated state, but in a state that does not cleave substrate in the plasma or blood. Upon addition of EDTA or other metal chelator, particularly a chelator or other agent that removes calcium ions, to blood or plasma, the activated MASP enzyme(s) cleaves its substrates. The enzymes, which were activated in vivo, are now available in vitro, and generate increases in products, such as C3a, C4a and C5a. This in vitro activity is in essence an artifact of taking blood into EDTA (or other divalent metal ion chelator), which removes calcium from the MBL-MASP complex, such that activated MASP cleaves its substrates, leading to increasing levels of C3a and C4a. Consequently, when C3a and C4a levels are measured as a means to assess classical and alternative pathway activities, in vitro activation is problematic. As shown herein, however, this in vitro activation, whose cause was previously unknown, reflects the amount of activated MASP enzyme in the plasma.

The observed in vitro activation provides a means to measure MASP activity and thereby assess in vivo lectin pathway stimuli or activators. In addition it provides a means to eliminate it and the accurately assess circulating levels of C3a, C4a and C5a. Inhibition of MASP enzyme(s), permits accurate measurement of the C3a, C4a and C5a levels and, hence, an indication of the level of activation of the classical and/or alternative pathways.

Addition of a serine protease inhibitor, such as Futhan, to EDTA plasma inhibits MASP enzymes and thereby eliminates the in vitro activation. Futhan addition to EDTA plasma prevents in vitro activation thereby permitting assessment of in vivo circulating levels of C3a, C4a, and C5a.

Parameters for using Futhan or other such serine protease inhibitors, along with EDTA or other metal chelator, as an effective additive for preventing complement activation during routine handling and processing of blood and plasma samples are provided herein. As shown herein, the combination of a serine protease inhibitor and a metal chelator, such as Futhan and EDTA, is effective when in vitro C-activation is relatively high, thereby establishing clinical utility of the procedure.

Addition of a serine protease inhibitor, such as Futhan, to plasma or blood, particularly to EDTA plasma or plasma containing another suitable chelator, permits it to be collected and either stored or shipped for later processing and analysis. The ability to stabilize complement in frozen plasma samples, or at 4° C., for more than 24 hours permits research and clinical samples to be analyzed for either total complement component levels or for of the C-activation fragments C3a, C4a and/or C5a.

As exemplified herein, when applied to patient blood samples, the Futhan/EDTA blood drawing protocol provided evidence that circulating C3a and C4a levels in liver (allograft) transplant patients were significantly elevated compared with control (i.e. "normal") individuals. None of these patients were experiencing acute rejection episodes and were considered to be doing well clinically on their respective treatment regimens. The more striking result was that conversion of C3 and C4 versus time was markedly higher in EDTA-blood or plasma from these patients than in the plasma from normal individuals. Therefore, in vivo MASP activity, assessed in Futhan/EDTA (or other serine protease inhibitor/chelator) plasma, serves as a sensitive parameter for assessing classical or alternative pathway activation. MASP activity, thus, is a sensitive parameter for assessing lectin pathway activation, such as occurs following organ transplantation.

Also provided are methods of assessing the efficacy of therapeutic treatments of mammals, particularly humans, for infectious agents, organ transplant rejection, tissue injury, autoimmune diseases and inflammatory responses in which C activation is mediated or initiated by exposure of neutral sugars. These methods involve obtaining a first sample of EDTA (or other suitable chelator, such as citrate) plasma from a subject prior to commencing treatment or after commencing treatment, determining mannan-binding protein-associated serine protease (MASP) activity in the first sample, obtaining a second sample of EDTA plasma from the subject after commencing treatment and at a time subsequent to the first sample, determining MASP activity in the second sample, and comparing the activity of MASP in the samples. A reduction in MASP activity reflects the efficacy of the selected treatment.

Methods for assessing the toxicity of or injury from therapeutic treatments are provided. To practice the methods a first sample of EDTA (or other suitable chelator, such as citrate) plasma is obtained from a mammalian, particularly, a human subject prior to commencing treatment or after commencing treatment, which is then followed by determining mannan-binding protein-associated serine protease (MASP) activity in the first sample, obtaining a second sample of EDTA (or other suitable chelator, such as citrate) plasma from the subject after commencing treatment and at a time subsequent to the first sample, determining MASP activity in the second sample, and comparing the activity of MASP in the samples. An increase in MASP activity reflects the toxicity of the treatment or injury from the treatment.

Methods for screening test compounds as agents for treatments of viral diseases, parasitic infections, tissue injury, organ transplant rejection, autoimmune diseases or inflammatory responses are provided. The methods include the steps of obtaining a first sample of EDTA (or other suitable chelator, such as citrate) plasma from a test animal model for a selected condition or disorder prior to administering the test compound, determining mannan-binding protein-associated serine protease (MASP) activity in the first sample, administering the test compounds, obtaining a second sample of EDTA plasma, determining MASP activity in the second sample, and comparing the activity of MASP in the samples. A decrease in MASP activity is indicative of activity of the test compound for the selected condition or disorder. In all of these methods, MASP activity can be assessed by measuring in vitro activation as a function of time, or by taking a single measurement (providing that it is taken at a time when the increase is linear) and comparing it to a control, such as the level of activation in a healthy or normal plasma sample.

Similar methods in which circulating levels C3a, C4a and C5a are measured are provided. These are performed by measuring the levels of each in blood or plasma in the presence of an inhibitor of serine protease activity. Thus provided are methods for diagnosing conditions associated with the classical or alternative pathway, to screen for drugs for treatment of such conditions and test therapeutic efficacy (or harm) for a particular treatment. In such methods, plasma is drawn into a serine protease inhibitor to inhibit in vitro activation mediated by MASP enzymes. C-activation, such as the levels of or rates of increase of C3a and C4a are measured. The amount of activation and type of activated components reflects which pathway is activated and thereby the type of agent responsible for the in vivo activation of the pathway(s).

DESCRIPTION OF FIGURES

FIG. 1B depicts the three activation pathways of the complement system, the relationships among the pathways, and shows that the MBP-MASP, where MASP refers to MASP-1 and MASP-1) is activated by carbohydrates (neutral sugars).

FIG. 3 sets forth an exemplary organ transplant panel, depicted is a liver transplant immunoassay panel provided herein for diagnosing acute rejection, viral infection, immune injury, incipient rejection and bacterial infection; included among the tests are the MASP test provided herein, which as shown in the Figure has high predictive value for various outcomes and will enhance a panel of known tests.

DETAILED DESCRIPTION OF PREFERRED EMBODIMENTS

A. Definitions

Figure 1A:
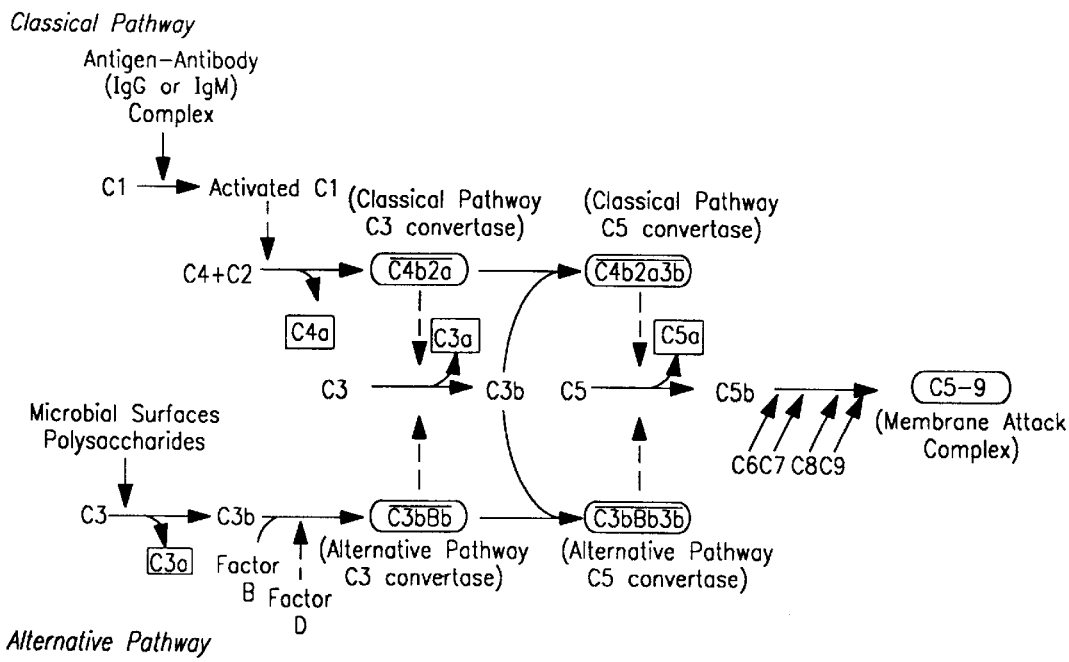
FIG. 1A depicts the classical and alternative (alternate) pathways of complement activation.

Unless defined otherwise, all technical and scientific terms used herein have the same meaning as is commonly understood by one of skill in the art to which this invention belongs. All patents and publications referred to herein are incorporated by reference.

As used herein, MBP (mannose binding protein) is also designated mannose-binding lectin (MBL).

As used herein, an inhibitor that specifically inhibits mannan-binding protein-associated serine protease (MASP), inhibits the activity of a MASP, but does not substantially inhibit the activity of other enzymes in the complement activation pathways.

As used herein, CR1 is complement receptor type 1, which is the C3b/C4b receptor. Complement receptor 1 (CR1 or CD35) is found on erythrocytes as well as a select group of leukocytes, including lymphocytes, neutrophils, and eosinophils. CR1 is a 190–280 kDa transmembrane protein that triggers the proteolytic degradation of membrane bound C3b molecules with which it comes in contact. It also promotes the clearance of immune complexes.

As used herein, C-activation refers to activation of complement pathways.

As used herein, cell activation refers to changes in and interactions among circulating white blood cells, including leukocytes, cells lining blood vessels, including endothelial cells, and platelets. These changes are evidenced by increased "stickiness" of cells, changes in shapes of cells, free radical production and release of inflammatory mediators and enzymes. Activated cells project large pseudopods, and express adhesion molecules on their surfaces. For example, adhesion molecules and villi attach macrophage and monocytes to endothelium. Macrophage and monocytes may then infiltrate into tissue outside the blood vessel beginning the development of atherosclerosis, venous insufficiency ulcers and diabetic retinopathy.

Cell activation is necessary for normal human immune defense mechanisms, but inappropriate or excessive activation leads to or participates or intensifies many diseases, including, but not limited to: arthritis, atherosclerosis, acute cardiovascular incidents, Alzheimer's Disease, hypertension, diabetes, venous insufficiency, autoimmune disease and others. Cell activation is a major contributor to rejections processes in organ transplants, and to predisposition for poor outcomes in trauma and high risk surgeries.

For example, LPS (lipopolysaccharide) binds to immunoglobin M and this complex activates the complement system with the release of C3b, which material in turn activates the polymorphonuclear leukocytes (PMN), monocytes, neutrophils, macrophage and endothelial cells. The activation of these substances stimulates the release of several mediators of septic shock including tumor necrosis factor (TNF-$\alpha$), interleukin-1 (IL-1) and other interleukins including IL6 and IL-8, platelet-activating factor (PAF), prostaglandins and leukotrienes (see, e.g., (1991) *Ann. Intern. Med.* 115: 464–466 for a more comprehensive listing). Of these, the two cytokines TNF-$\alpha$ and IL-1 lead to many of the physiologic changes which eventuate into septic shock.

The LPS-stimulated macrophages also release other free-radicals, including free-radicals from arachidonic acid metabolism, which can also cause extensive damage to endothelial cells. These lead to aggregation and circulatory collapse, which in turn leads to hypotension, tissue damage, multi-organ failure and death. Thus, excess production of the above mentioned free-radicals is linked to the mortality associated with septic shock.

As used herein, polymorphonuclear leukocytes (PMNs). Polymorphonuclear neutrophil granulocytes (PMN) are cells which are mobilized during inflammatory phenomena and which can be stimulated by various compounds, such as, for example, C5a, formylmethionyl-leucyl-phenylalanine (FMLP) or prostaglandins E (PGE1). The PMN granulocytes respond to these extracellular stimuli with an activation of oxygen metabolism and release of toxic oxygenated metabolites. An excessive response of the PMN granulocytes may be the cause of a painful inflammation and is also accompanied by a reduction in the level of cyclic adenosine monophosphate (cAMP) in these granulocytes.

As used herein, EDTA plasma refers to plasma produced from blood drawn into standard containers, such as tubes that contain EDTA. For examples, tubes containing about 5 mg of $Na_2$-EDTA were designed for collecting 2.5–5.0 ml of blood. It is understood that other suitable chelating agents, particularly calcium ion chelators, can be used in place thereof. Such agents include, but are not limited to: citrate, polycarboxylic acid chelating agents, such as alkylene polyamine polyacetic acids of the formula $(HOOCCH_2)2N[(CH_2)_nN(CH_2COOH)]_mCH_2COOH$, where n is 1,2,3 or 4 and m is 0,1,2,3, or 4, up to two of the carboxymethyl groups may be replaced with a beta-hydroxyethyl group and one or more of the carboxymethyl groups may be replaced by carboxyethyl groups. Specific examples of such polyacetic acids which are particularly suitable include N-hydroxyethylethylenediaminetriacetic acid, nitrilotriacetic acid, N-2-hydroxyethyliminodiacetic acid, diethylenetriamine-pentaacetic acid, and mixtures thereof.

As used herein, treatment means any manner in which the symptoms of a conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein an effective amount of a compound or composition for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, a control refers to a sample that is substantially identical to the test sample, except that it is not treated with a test parameter, or, if it is a sample plasma sample, it may be from a normal volunteer not affected with the condition of interest. A control may also be an internal control.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726). C3a and C4a, fragments called anaphylatoxins that are generated from complement components C3 and C4, respectively; CMV, cytomegalovirus; $\gamma$GT, gamma-glutamyl transferase; CsA, cyclosporine A, FK506 (a well known macrolide antibiotic isolated from the fungus *Streptomyces tsukubaensis* by the Fujisawa Pharmaceutical Company of Japan, see, e.g., U.S. Pat. Nos. 5,807,876, 5,100,899, and 5,164,495); SGPT, aspartate aminotransferase; SGOT, alanine aminotransferase; CR1, complement C3b receptor; Futhan, 6-amidino-2-naphthyl-p-guanidinobenzoate dimethanesulfonate; MASP-2, MBL (mannan-binding lectin)-associated serine protease-2; and EDTA ethylenediaminetetraacetic acid.

Diagnosis Using Complement Activation

The complement system is a fundamental element of normal host defense mechanisms. As a consequence, complement activation is commonly associated with a variety of pathological states such as certain malignancies, myocardial infarction, systemic lupus erythematosus, and adult respiratory distress syndrome. Because of these correlations clinical laboratory methods that detect complement activation are useful in diagnosing certain disease conditions. Unfortunately, as noted above, because of in vitro complement activation, accurate in vivo measurements of the classical and alternative pathways are difficult to obtain. Furthermore, methods for assessing activity of the lectin pathway are unavailable. Methods for assessing, including detecting and monitoring, the activation level and activity of these various pathways are provided herein. For example, activation of activation classical pathway is associated with certain disorders, including inflammatory responses, such as those seen in Alzheimer's disease and bacterial diseases.

Thus, methods for monitoring disorders and conditions associated with in vivo activation of the classical and alternative pathways are provided. In these methods, the activity of MASP is inhibited in EDTA plasma, thereby permitting accurate measurements of components of the complement pathways, particularly the classical and alternative pathways.

It is shown herein that the MASP enzymes, MASP-1 and/or MASP-2, are responsible for the ex vivo (i.e., in vitro) activation of complement that is observed in EDTA plasma or plasma containing any metal chelator, particularly calcium chelators, including citrate. The metal ion chelator, such as EDTA in the plasma, removes calcium ion, thereby permitting MASP to act in the fluid phase, which artificially alters C3a and C4a levels in the plasma.

MASP activity is measured by measuring C3a and C4a levels in in vitro activated plasma, containing a metal chelator, such as EDTA or citrate, using standard methods, such as a commercially available kit, as index of the enzyme activity. The increase in C3a and C4a as a function of time or the relative amount of either compared to a control or standard is an indicator of the amount of activated MASP in the plasma at the time the blood from which the plasma is obtained was drawn.

These methods are performed by measuring increases in C3a and C4a levels, particularly C4a, in plasma in the presence of a metal chelator, such as EDTA or citrate, which removes divalent metal ions, particularly calcium. C3a and C4a are measured using any method, such as immunoassays, known to those of skill in the art.

Knowledge of the origin of in vitro activation provides a means to eliminate it, such as when it is desired to measure C3a, C4a and C5a levels to assess in vivo alternative and in vivo classical pathway activation. This can be achieved by inhibiting MASP activity, which is responsible for the observed in vitro activation. As shown herein, serine protease inhibitors, such as Futhan (6-amidino-2-naphthyl-p-guanidinobenzoate dimethanesulfonate), are direct inhibitors of MASP-2 or MASP-1, and, thus provides a means to obtain stable samples in which no further C3 or C4 conversion occurs as a result of activated MASP activity.

Methods for assessing the circulating levels of C3a and C4a are also provided. To accurately measure C3a and C4a levels in plasma in vivo, MASP activity in the EDTA is inhibited, such as by the serine protease inhibitor Futhan (6-amidino-2-naphthyl p-guanidinobenzoate dimethanesulfonate), thereby inhibiting in vitro complement activation. Thus, provided herein, is a method for evaluating activation of the alternative and/or classical pathways without interference from the lectin pathway. In an embodiment of this method, a EDTA plasma sample from a mammal is obtained; an effective amount of a MASP-specific inhibitor, particularly Futhan, is added, where the amount inhibits substantially all MASP activity exposure of the MBL-MASP complex to a chelator, and levels of C3a or C4a are measured. Generation of C4a signals conversion of C4, which is indicates activation of the classical pathway. Formation of C3a in the absence of C4a indicates activation of only the alternative pathway.

Since each pathway is activated by distinct activators, identification of the activated pathway reflects the mode of activation. Activation of the classical pathway involves immunoglobulins or immune complexes. The alternative pathway is activated by infectious agents, such as bacteria or yeast, particularly in the early stages of infection before antibodies are formed.

Lectin Pathway

Methods for monitoring the lectin pathway components are provided. In particular, a method for monitoring MASP activity in plasma is provided. In the method, in vitro complement activation is assessed as a function of time. Since, as shown herein, this activity is observed in the presence of divalent metal chelators, and, thus, results from removal of calcium and/or other divalent ions from the complex containing of activated MASP, particularly activated MASP-2, the in vitro complement activation, as measured by detecting and monitoring formation of components, such as C4a and/or C3a, can be correlated with MASP activity in the original sample. The activity can be quantitated for example, by measuring C4a at time 0, and as a function of time. The rate of increase and/or the magnitude of the increase in activity reflects MASP activity. The particulars of such determination can be determined empirically. C4a, C3a and other components can be measured using methods well known to those of skill in the art, such as radioimmunoassays (RIAs), enzyme immunoassays (EIAs), including those that are commercially available.

Thus methods for detecting and monitoring conditions and diseases associated with the lectin pathway, including but not limited to, tissue and organ injury, particularly transplanted organs and tissues, and viral and parasitic infection are provided.

Figure 1B:
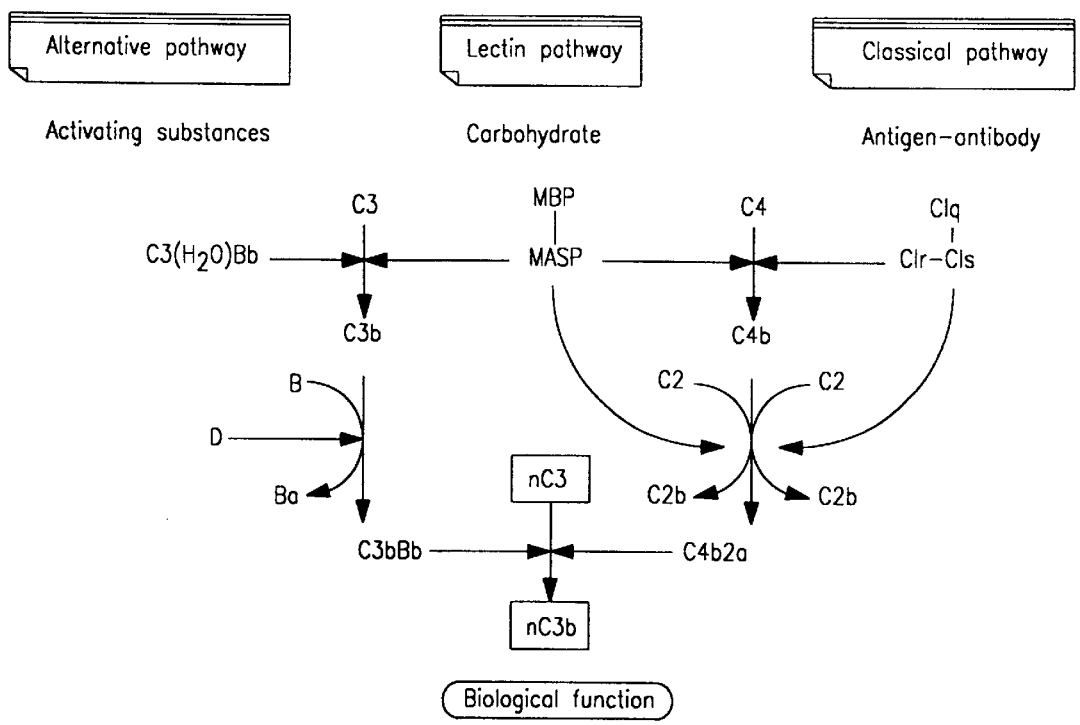
FIG. 1B provides an overview of the classical and alternative pathways, which converge at the C3 convertase step leading to C5 cleavage and self assembly of the membrane attack complex (MAC), and shows the classical pathway, which is initiated by C1 binding to antigen-antibody complexes or aggregates of immunoglobulins, and the alternative pathway, which is initiated in several ways, including spontaneous cleavage of a thioester, by amino groups, hydroxyl groups, and water; bars over the complexes designate enzymatic activity and the products in boxes are anaphylatoxins (see, Ember et al. (1997) *Immunopharmacology* 38:3–15)

MBL binds to a variety of microorganisms, coating the targets with activated C4 and activated C3, making them accessible to phagocytic cells that carry these molecules. MBL recognizes complex carbohydrate structures, particularly neutral sugars, and interacts with two associated proteases, MASP-1 and MASP-2. It appears that activated MASP-2 is responsible for C4 cleavage, thus, integrating MBL into the complement system at the C4 activation step (see, e.g., FIG. 1). MASP activation is implicated not only responses to microorganisms, but in any response that involves exposing neutral sugars, including by not limited to tissue injury, such as that observed in organ transplants. Thus, monitoring MASP activity, provides means to monitor microbial, particularly parasitic, infections, viral infections, particularly CMV (cytomegalovirus), hepatitis virus (HbA and HbB), and HIV infection, and acute and chronic organ rejection.

Futhan and the Lectin Pathway

Amidines and guanidine derivatives will inhibit complement-mediated hemolysis (i.e. C-activation; see, Otterness et al. (1978) *Biochem Pharmacol* 27:1873–1878). Based in part on this information, a potent synthetic inhibitor of complement and coagulation proteinases 6-amidino-2-naphthyl-4-guanidinobenzoate dimethanesulfonate (trade name Futhan or FUT-175; generic name nafamostat mesilate, which is 6-amidino-2-naphthyl p-guanidinobenzoate dimethanesulfonate) was designed, synthesized and characterized (see, Fujii et al. (1981) *Biochim.Biophys.Acta* 661:342–345). This proteinase inhibitor has a broad specificity for serine proteases, and is a potent inhibitor of coagulation and complement proteinases. Futhan inhibits thrombin, plasmin and kallikrein (plasma and pancreatic), all of which can degrade complement components C3, C4 and/or C5 (Hugli (1977) in Chemistry and Biology of Thrombin, Lundblad et al., Eds. p. 345, Ann Arbor Science, Ann Arbor, Mich.; Pfeiffer et al. (1997) in Techniques in Protein Chemistry VIII Techniques in Protein Chemistry VIII, Marshak, Ed., pp. 363–369, Academic Press, San Diego). Studies have focused on identifying complement proteinase targets of Futhan, which include C1r, C1s, Factor B, and D (Ikari et al. (1983) *Immunology* 49:685–691). This inhibitor is also effective toward Hageman factor and Factor Xa at the sub-micromolar level (Hitomi et al. (1985) *Haemostasis* 15:164–168). Several studies have examined the in vivo protective effects of Futhan in various models of immunological reactions including Forssman shock in guinea pigs, passive cutaneous anaphylaxis in rats, and delayed hypersensitivity reactions and endotoxin shock in mice (Hitomi et al. (1982) *Int.Arch.Allergy Appl.Immunol.* 69:262–267; Iwaki et al. (1986) *Japan J.Pharmacol.* 41:155–162). Since Futhan inhibits complement-mediated hemolysis by the alternative and classical pathways (Watkins et al. (1989) *Lancet* 1:896–897), it was concluded that the major effect of this compound on in vivo immunological reactions resulted from direct inhibition of enzymes in the C-activation pathways.

Studies have been undertaken to characterize Futhan activity in vivo and to identify the various proteases that it inhibits. It has been shown that Futhan effectively stabilizes freshly drawn blood samples from normal individuals permitting direct measurement of the anaphylatoxins C3a and C4a (Pfeiffer et al. (1997) in Techniques in Protein Chemistry VIII Techniques in Protein Chemistry VIII, Marshak, Ed., pp. 363–369, Academic Press, San Diego).

In EDTA Plasma, EDTA Activates MASP Activity

Complement is not stable in plasma that contains a metal chelator, such as EDTA or citrate or other chelator, particular chelators that remove calcium ions, over time. Numerous earlier attempts to stabilize complement in blood or plasma have been reported. The most successful procedure to date involve the use of a broad-spectrum serine proteinase inhibitor called Futhan (Ikari et al. (1983) *Immunology* 49:685–691; Hitomi et al. (1985) *Haemostasis* 15:164–168; Hitomi et a. (1982) *Int.Arch.Allergy Appl.Immunol.* 69:262–27; Iwaki et al. (1986) Japan *J.Pharmacol.* 41:155–162; Watkins et al. (1989) *Lancet* 1:896–897). The mechanism of action of Futhan, however, was not understood.

A goal herein is to provide a protocol for blood or plasma collection and handling that can effectively stabilize complement, even in patient blood samples where in vitro C-activation was known to be extensive. Previous studies using Futhan to prevent C-activation focused primarily on normal blood samples. In normal blood or plasma held at 4° C., significant activation of C4 versus time even in the presence of EDTA was observed. There was little conversion of C3 in normal EDTA blood or plasma, even up to 24 hrs, indicating that the proteinase responsible for C4a generation is selective for C4 cleavage over C3. Adding 0.01 mg/ml Futhan to the EDTA plasma resulted in measurable reduction in C4 conversion versus time and 0.10 mg/ml of Futhan virtually eliminated C4 cleavage over a 24-hour period. Since 0.10 mg/ml Futhan was the concentration of the inhibitor used in the commercial Futhan/EDTA blood drawing tubes, many of the experiments were performed using this level of the inhibitor.

It is shown that the combination of Futhan and EDTA in blood or plasma stabilizes the C4 over a 24 hr period. The results described herein demonstrate that blood or plasma samples can be drawn at one site and shipped overnight either on ice or frozen to another site for analysis.

Since Futhan is a serine proteinase inhibitor that inhibits coagulation proteinases, as well as complement proteinases, several other proteinase inhibitors that inhibit proteinases in blood systems were examined. Benzamidine and Trasylol (Kunitz's inhibitor) were relatively effective in preventing C4 conversion in whole blood over 60 min., but C3 was converted. These inhibitors, thus, are more effective blockers of the serine proteinase Factor I than Factor B. Factor I is a control proteinase that inactivates C3 convertase (C3b, Bb) by cleaving the essential cofactor C3b to C3bi thereby destroying the active enzyme complex. Therefore, if Factor I is inhibited, small quantities of C3b, Bb will be formed in blood and permit the alternative pathway to progress unimpeded. When EDTA was added to these same blood samples, C3 conversion by the $Ca^{++}$-dependent classical and alternative pathways was prevented. C4 conversion in the presence of EDTA indicated possible activation of the lectin pathway. Neither of the coagulation proteinase inhibitors were effective in blocking C4 conversion. Futhan appears to be fully effective in inhibiting this proteinase.

The methods provided herein are based upon these findings and those set forth in the EXAMPLES. Key among these are the results depicted in FIG. 2, which shows that EDTA is the activator of the MASP activity in EDTA plasma. As shown in the figure, for example, when the benzamidine, a coagulation inhibitor is added, there is no C4a generated in whole blood, but upon addition of EDTA, high levels of C4a are generated. Since benzamidine blocks the alterative and classical and coagulation pathways but does not inhibit MASP activity, the high levels of C4a generated are attributable to activated MASP, particularly MASP-2, present in the MBL complex, and rendered active upon contact with EDTA. Thus, the increase must attributed to MASP activity generated in the presence of EDTA. As shown in the figure, Futhan inhibits MASP. Therefore, even in EDTA, no MASP activity is observed.

In addition, it is noted that the data set forth in this figure was obtained with blood from healthy individuals, not blood from patients. In patient blood, measurement of MASP-generated C4a produces a large signal, demonstrating the diagnostic potential of such an assay.

It is shown herein that the proteinase responsible for the in vitro activation of C4 is the MASP-2 enzyme of the lectin pathway (Thiel et al. (1997) *Nature* 386:506–510). As shown herein, the MASP-2 enzyme of the lectin pathway is primarily responsible for in vitro C-activation (See Table II, below).

Thus, assessing MASP activity provides a status of abnormality, to assess exposure to viruses and parasites, tissue injury or anything that leads to exposure of neutral sugars. Assays of MASP activity can be used for evaluating blood units drawn in blood banks to identify virally (or parasitically) infected blood samples. They also can be used to monitor patient conditions, such as viral, parasitic infections and other diseases, and for longitudinal monitoring to detect changes in status, such as those exemplified herein in organ transplant patients.

As shown in the EXAMPLES, it was found that the Futhan/EDTA plasma samples from liver transplant patients (n=19) at 0 time was already elevated at 1.76 μg/ml and rose to 13.8 μg/ml C3a after 60 min. at rt. Corresponding values for C3a in Futhan/EDTA plasma from these same patients at 0 and 60 min. were significantly lower at 1.40 and 2.02 µg/ml, respectively. The average level of C4a in EDTA plasma from these patients were 4.02 µg/ml at 0 time, which rapidly rose to 16.9 µg/ml after 60 min. at rt. The average C4a levels in Futhan/EDTA plasma from these patients at 0 and 60 min. were only 0.83 and 0.94 µg/ml, respectively. This data indicated that Futhan controlled in vitro C-activation and that the C3a and C4a levels in patient EDTA plasma was markedly elevated compared to that in normal individuals. Neither the coagulation cascade nor the classical or alternative complement pathways function in the presence of EDTA.

Therefore, MASP-2 of the lectin (i.e. third) pathway of complement must be cleaving the C3 and C4 in EDTA plasma samples. These results demonstrate that adding EDTA to blood, activates the plasma enzyme. The inhibitor Futhan, but not benzamidine or Trasylol, fully blocked in vitro C-activation, presumably by inhibiting the MASP-2 proteinase. Consequently, the circulating levels of either intact C-components (i.e. C3, C4 and C5) or the activation factors C3a and C4a can be accurately and reliably measured in Futhan/EDTA, but not in EDTA plasma, without significant elevation of either C3a or C4a levels.

Therefore, MASP enzyme is responsible for in vitro complement activation. Measurement of the activation reflects the amount of activated MASP in a blood or plasma sample. The amount of activated MASP reflects the immune response of a patient, particularly exposure of the MBL-MASP complex to neutral sugars, such as those on a viral coat, a parasite, injured tissue and other such conditions.

Methods of assessing these conditions and measuring the amount or relative amount of activated MASP are provided. It can be measured by determining the rate of increase of the activated complement component(s) and compared to a standard or to the rate of increase in a sample from a normal individual not exhibiting substantial MASP activation.

It is shown herein, that complement activity increases substantially linearly as function of time in a plasma or blood sample. The rate of increase is directly proportional to the amount of activated MASP. In addition, it is shown herein, where MASP activation is observed, such in transplant patients experiencing infection or early stages of rejection, the amount of C4a or C3a produced in vivo is substantial and far greater than the circulating amounts. Thus, at a selected time point, the a single measurement of MASP activity is indicative of the level thereof. Thus, for purposes herein MASP activity can be assessed by measuring the amount of C4a and/or C3a as a function of time or a single time point selected from at least the middle of the linear portion of an activity versus time curve. MASP activity may also be determined as a relative amount at a particular time point, which time point is selected to be during the linear increase that is observed when a sample undergoes in vitro activation. Since the amount of C4a or C3a observed increases as a function of time, the contribution to the amount from MASP activity is high once the in vitro activation is underway. A particular time point, such as 10 minutes, 20 minutes or 30 minutes, depending upon the samples, can be selected empirically and MASP activity measured. It can be measured relative to the amount at time 0 or relative to the amount at the maximum. An absolute activity can be determined by comparison with a standard curve. Those of skilled in the art can readily determine suitable controls for a particular assay or suitable means to measure rate, relative amount, or absolute amount.

The assays of MASP activity can also be used to monitor effectiveness of therapeutics, such as antiviral treatments (for treatment of hepatitis B, C, CMV, HIV infections), antiparasitics, and tissue injury treatments by measuring the activity as therapy progresses and looking for decreases.

The assays may also be used to screen for effective drugs by monitoring MASP activity in model animal systems or even in humans. Drugs that are effective for MASP-associated disorders (i.e, those that induce MASP in vivo, such as coated viruses, parasites and tissue injury) will result in a lowering of the amount of MASP activity in plasma or blood containing a chelator, such as EDTA.

The assays may also be used to assess toxicity of certain therapeutics for MASP-associated disorders by looking for increases in MASP activity in blood or plasma, containing metal chelators.

In all instances, the level of MASP is assessed by measuring C4a, C3a or C5a levels in the presence of a metal chelator. These proteins are measured using assays (see Examples) known to those of skill in the art and also any that may be developed therefor.

Classical and Alternate Pathway Activation

It is the process of ongoing C-activation that prevents accurate analysis of intact complement components and their breakdown products in EDTA blood samples. As shown herein, elimination of the in vitro activation permits accurate measurements of circulating complement components, which reflect immune status of the subject mammal, including human, from whom the sample is taken. This can be achieved by inhibiting MASP activity, such as by adding a serine protease or any other agent that inhibits such proteases. Inhibition of MASP, then permits the assessment of alternative and classical pathway activation.

Activation of the classical pathway reflects immune activation or immune complexes; activation of the alternative pathway generally reflects exposure to bacterial pathogens because OH, and $NH_2$ groups activate the pathway.

As shown in the examples, and discussed above, metal chelators, such as EDTA and, serine protease inhibitors, such as Futhan, affect the complement pathways in a variety of ways. The manner in which the pathways are affected permits assessment and monitoring of different diseases and conditions. These results are summarized in TABLE II:

TABLE II

EFFECTS OF EDTA AND FUTHAN ON THE COMPLEMENT ACTIVATION PATHWAYS

| | Alternative Pathway | Lectin Pathway | Classical Pathway |
|---|---|---|---|
| I | bacteria, yeast, viruses, parasites ($NH_2$ and OH groups) | pathogens, viruses, injured host cells (neutral sugars) | $(IgG)_n$, IgM, CRP, Ag/Ab, polyanions |
| II | C3b, Bb | MBL/MASP-1 & 2 | C1q, r, s |
| III | +EDTA NO C-activation | +EDTA IN VITRO C-activation C4a≧C3a | +EDTA NO C-activation |
| IV | +FUTHAN | +FUTHAN | +FUTHAN |
| | NO IN VITRO C-ACTIVATION | | |
| | Only circulating levels of C3a, C4a and C5a are detected | | |

I: Common activators of various pathways; II: Enzyme complexes that initiate the C-activation cascades; III: Activities of the pathways in EDTA plasma; IV: Inhibition of all pathways (Futhan/EDTA) permits a true estimation of circulating levels of complement components and activation products in plasma samples.

The agents EDTA and the proteinase inhibitor Futhan have been used in combination, but their effectiveness in stabilizing blood and plasma samples from patients has not been fully characterized nor exploited. Provided herein is an understanding of the mechanism of action of these moieties and permits substitution of other agents therefor. Thus, other metal ion chelators, such as citrate can be used in place of EDTA, and other serine protease inhibitors can be used.

Furthermore, their use, singly or in combination, provides a means for monitoring the classical and alternative pathways and the lectin pathways, which has not heretofore been described. The methods herein exploit their use and also provide assays for monitoring in vivo activation of the classical and alternative pathways and the lectin pathways.

It is generally recognized that determination of C-activation in human blood samples is at best cumbersome and procedurally difficult to perform, and at worst unreliable. Complement is a system of more than 20 plasma proteins and these components represent three known activation pathways or cascades. Part of the reason for the unreliability of such measurements is the nature of the various tests. Measurement of blood level of the various intact complement components has been used to determine whether concentrations are in the normal or abnormal range, but this type of data fails to indicate whether ongoing C-activation is occurring. Measurement of various breakdown or activation products such as C3c, C3d, C4d and the C5b-9 complex have all been used to monitor on-going C-activation. If in vitro activation occurs, these measurements are often difficult to interpret and have various drawbacks, such as distribution problems (i.e. cell bound versus free). Catabolism or metabolism issues also arise.

The fragments C3a and C4a are good candidates to monitor activation. These fragments are smaller than most other molecules released during C-activation and are exceptionally stable. It is generally accepted that accurate measurement of circulating levels of the C3a and C4a molecules would have significant clinical applications in monitoring immune disease.

The primary advantages of measuring these two activation fragments of complement components C3 and C4 are: 1) C3a and C4a levels are direct indicators of the type and extent of activation, since C4a is only generated during classical or lectin pathway activation and C3a generation is the absence of C4a confirms alternative pathway activation; 2) The des Arg forms of C3a or C4a do not bind to specific cellular receptors and thus circulate freely without further degradation. Once C3a and C4a are released in the blood they are rapidly converted to the des arginine forms (C3a des Arg and C4a des Arg) by serum carboxypeptidase N (Bokisch et al. (1970) *J.Clin.Invest.* 49:2427–2436); 3) C3 and C4 are abundant blood proteins and even minor C-activation can be detected by a sensitive assay for these breakdown products; 4) the factors C3a des Arg and C4a des Arg are extremely stable proteins and are not denatured by handling; and 5) generation of these factors signals production of numerous physiologically important breakdown products of the complement cascade, namely C3a, C4a, C3b, C4b, C3bi, C4bi, C3d and C4d, each having known biologic functions or activities.

Figure 2:
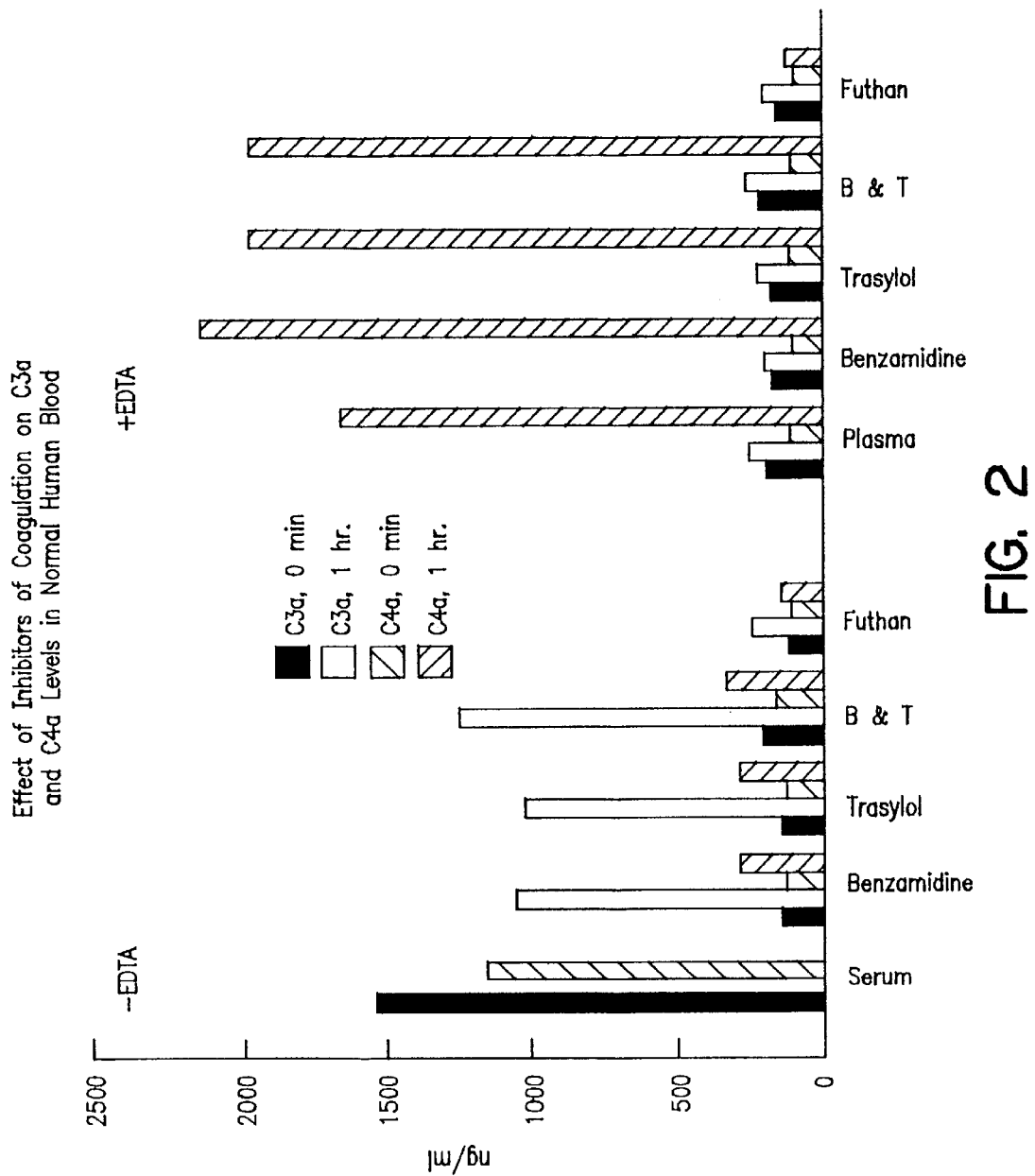
FIG. 2 shows the results of experiments in which complement activation in blood was measured in the presence of several anti-coagulants, with and without EDTA (0.5 mg/ml); whole blood from a normal donor was drawn into 0.15 mM Benzamidine, 20 $\mu$M Trasylol or 0.1 mg/ml Futhan and processed either immediately (0 time) or after 60 min.at rt., then analyzed for C3a and C4a; Benzamidine and Trasylol failed to prevent C3a generation in these blood samples, while Futhan was an effective inhibitor; when these same additives were combined with 10 mM EDTA there was no generation of C3a, however, except when Futhan was present, extensive conversion of C4 occurred, thereby indicating that MASP activity is responsible for the C4 conversion.

Based on the results in FIG. 2 (see discussion above and the EXAMPLES), Futhan/EDTA plasma, but not whole blood, can be collected and stored for at least 24 hours. The EDTA/Futhan plasma provides an appropriate sample for obtaining reliable circulating levels of C3a and C4a (or C3 and C4) while avoiding in vitro activation that would render the data invalid.

In the experiments described in the EXAMPLES, the C3a values (n=20) were 0.60+/−0.026 and 0.45+/−0.018 µg/ml respectively, in normal EDTA plasma and in Futhan/EDTA plasma stored at 4° C. for 24 hours. Corresponding C4a levels were 0.32+/−0.017 in EDTA plasma and 0.19+/−0.011 µg/ml in Futhan/EDTA plasma. These data indicated that C3 and C4 were somewhat more activated in EDTA plasma than in Futhan/EDTA, even during careful handling of normal plasma.

Assays for Measuring C3a and C4a and other Complement Components

Numerous assays are known and available for measuring complement components. Heretofore, no methods to accurately assess in vivo levels were known. The methods herein provide means to accurately assess in vivo levels of these components.

As noted herein, and exemplified below, numerous assays, including RIAs and EIAs are known and available for measuring these components (see, e.g., U.S. Pat. No. 5,778,895, U.S. Pat. No. 4,731,336, see, also, Hugli et al. (1975) *J. Biol. Chem.* 250:1472–1478; Hugli (1975) *J. Biol. Chem.* 250:8293; and Hugli et al. (1981) *J. Biol. Chem.* 256:2685–2692). Kits for performing the assays are commercially available.

The results herein that show that inhibition of MASP activity in plasma permits accurate determination of complement components, permits the associated disorders to be monitored. Thus, the known methods for measuring these components are modified herein, by including a step in which MASP activity in plasma is inhibited, such as by drawing the blood into a serine protease inhibitor.

In addition, methods for assessing in vivo MASP activity are provided. Measurement of complement components, particularly C4a and/or C3a, either compared to standards or controls or as a function of time, in plasma containing a metal chelator, such as EDTA, can be correlated with in vivo MASP levels. Alternatively, a selected time point where activity has increased, can be selected and compared to a standard or normal control.

Practice of the Methods to Assess Status in Patients with Organ Transplants

Assessment of MASP activity and complement components, such as C3, C4a and C5a, in conditions, such as the onset of rejection and infections associated with organ transplantation, is provided as exemplary of the conditions that can be monitored using the methods provided herein. In addition, the results from these experiments, which are described in detail in the EXAMPLES, demonstrate that MASP activity is responsible for in vitro complement activation.

Despite continued improvements in patient and graft survival (Gordon et al. (1986) *Surgery* 100:705–715), several complications may occur in liver transplant patients that lead to graft dysfunction and rejection (Adams et al. (1990) *J. Hepatol.* 10:113–119). Even though cellular immune responses appear directly responsible for acute allograft rejection, acute and chronic rejection may be enhanced through complement activation. Among other consequences, involvement of complement and generation of activated components in patients with grafted organs may result in enhanced inflammatory responses leading ultimately to severe damage of the organ (Baldwin et al. (1995) *Transplantation* 59:797–808). Some complement activation data exists for renal transplant patients at the level of tissue C3d and C4d deposition (Feucht et al. (1991) *Clin. Exp. Immunol.* 86:464–470); Feucht et al. (1993) *Kidney Int.* 43:1333–1338), and circulating levels of the anaphylatoxins from patients experiencing acute renal disease have been reported (Abou-Ragheb et al. (1991) *J. Clin. Lab. Immunol.* 35:113–119). There are virtually no longitudinal complement activation data for renal or liver transplant patients beyond the immediate post-operative reperfusion phase where C3a and C5a levels were observed to be significantly elevated (Ronholm et al. (1994) *Transplantation* 57:1594–1597; van Son et al. (1987) *Am. Rev. Respir. Dis.* 136:580–585).

The immunosuppressed patient is susceptible to recurrent bacterial infections, which in turn primarily activate C3 via the alternative complement pathway, and is susceptible to viral infections that involve primarily the classical or lectin pathway (Epstein et al. (1996) *Curr. Opin. Immunol.* 8:29–35; Reid (1998) C1q and mannose-binding lectin. The human complement system in health and disease, Volanakis et al. eds., New York: Marcel Dekker, Inc., 3, p. 33–48). Consequently, immune activation of the classical or lectin pathway is easily distinguished from bacterial infection episodes simply by monitoring elevations in C4a levels. Transplant-specific complications in liver function are monitored through organ-specific plasma enzymes such as gamma-glutamyl transferase or metabolites such as bilirubin. Often, the pathologic condition of the organ must be confirmed through tissue biopsy (Bronsther et al. (1988) *J. Med. Virol.* 24:423–434; Snover et al. (1987) *Am. J. Surg. Pathol.* 11:1–10), causing significant discomfort to the patient, as well as increased expense and considerable risk.

Reliable detection of certain relatively common complications in transplant patients, such as recurrent hepatitis or CMV infection in liver transplant patients, remains difficult to recognize early in their course. A reliable non-invasive detection system capable of efficiently identifying these non-rejection events, as well as methods for monitoring immune injury or efficacy of anti-virals or the efficacy of immunosuppressive regimens, is currently not available.

Considering that most of the late rejection episodes in liver transplant patients (occurring more than 6 months after transplant) are associated with subtherapeutic levels of cyclosporine (Mor et al. (1992) *Transplantation* 54:821–824), and in view of the toxic side-effects of this drug (Mason (1989) *Pharmacol. Rev.* 42:423–434), it would be desirable to have a diagnostic/monitoring system for optimizing conventional immunotherapies for liver transplant patients as well as patients transplanted with other organs. Such a system is provided herein.

In vitro Complement Activation Reflects Lectin Pathway Activity

As shown in EXAMPLE 2, the C-activation profiles of complement versus time in liver transplant patients indicates that pathologic events such as acute rejection episodes, hepatitis B, hepatitis C or CMV viral infections, as well as bacterial infections can be detected by monitoring MASP activity. Many of the events monitored in these patients appear to involve primarily the classical and lectin pathways (i.e., only C4a levels were elevated). Other immune diseases, particularly autoimmune diseases such as SLE and rheumatoid arthritis can be monitored effectively by following C4a levels or MASP activity, particularly MASP-2, enzyme, in EDTA (or other metal chelator, such as citrate) plasma and/or determining the circulating C3a and C4a levels in Futhan/EDTA plasma samples as described herein.

Baseline values of C3a/C4a in these transplant patients may be slightly elevated due to in vitro complement activation that occurs in these EDTA blood samples versus time (Watkins et al. (1989) *Lancet*:896–897). All samples were collected locally under carefully controlled conditions (i.e. in EDTA-blood stored immediately on ice) and so the 0 time values are not be markedly affected by in vitro activation. The blood samples were collected in EDTA and the plasma was immediately recovered. The 0 time plasma samples (5 ml) from each donor were then processed immediately to remove the parent compounds C3 and C4 and to prevent further activation. A separate set of EDTA plasma samples were incubated 60 min. at room temperature. C3a and C4a levels were determined in each of these samples. The average C3a and C4a levels in the 11 non-transplant and 19 transplant patients are reported as ng/ml of plasma.

A notable finding was that incubation of the EDTA plasma from the liver transplant patients resulted in extensive in vitro activation of complement compared to normal non-transplant individuals. The C3a and C4a levels were determined in EDTA plasma obtained from 11 normal individuals and 19 liver transplant patients during routine visits. These patients were not having a rejection episode.

Blood from the same nineteen liver transplant patients was collected in 0.5 mg/ml EDTA alone. C3a and C4a levels were determined at 0 time and after 1 hr at room temperature. Extensive in vitro complement activation was observed in a group of these patients as evidenced by the elevation of C3a and C4a following incubation. The plasma from patients who did not show signs of significant in vitro activation still had C3a and C4a levels higher than average normal (n) values. Patient plasma that showed extensive C-activation were easily discerned and these samples are proposed to have elevated levels of MASP-2 activity.

The high level of in vitro activation of complement, thus is a useful indicator of organ status. The average C4a levels in the patient's EDTA plasma were markedly elevated versus time and this activity may offer an additional parameter for monitoring organ status in post-transplant patients. More than 16 $\mu$g/ml C4a was generated in transplant plasma after one hour at room temperature compared with less than 1 $\mu$g/ml C4a in normal EDTA plasma. Normal EDTA-plasma levels for C3a in this study compared favorably with published levels of C3a in fresh frozen plasma (FFP) (Sonntag et al. (1997) *Transfusion* 37:798–799). When FFP was thawed, the C3a levels rose to only 1.2 $\mu$g/ml (n=12 FFP) after 6 hours compared to nearly 14 $\mu$g/ml (n=11) of C3a generated in the liver transplant patient plasma after just one hour.

Consequently, abnormal in vitro complement activation in the plasma of transplant patients could be evaluated using either C3a or C4a levels as a detection assay. These results demonstrate that the in vitro activity is reflects lectin pathway (i.e., MASP, particularly MASP-2) function, since neither the classical or alternative pathways function in the presence of EDTA.

Addition of a Protease Inhibitor

Blood from nineteen liver transplant patients was collected in 0.1 mg/ml Futhan and 0.5 mg/ml EDTA. The C3a and C4a levels were measured at 0 time and after 1 hr at room temperature. These samples were obtained during routine visits by the patients having no signs of acute rejection episodes. Note that the levels of C3a and C4a were unchanged in most samples after 1 hr. of incubation at rt. The individual and average (Av) levels of C3a and C4a were considerably higher than the average value for n=20 non-transplant (n) individuals. Since Futhan prevents in vitro activation, it circulating levels of C3a and C4a are generally elevated in liver transplant patients.

The use of blood drawing tubes containing a broad spectrum protease inhibitors, such as Futhan and EDTA (Fujii et al. (1981) *Biochim. Biophys. Acta* 661:342–345; Ikari et al. (1983) *Immunology* 49:685–691; Watkins et al. (1989) *Lancet*:896–897) will make measurement of the complement products actually generated in vivo (i.e. circulating levels) versus in vitro levels even more reliable since all three complement pathways are inhibited by Futhan. On the other hand, since the liver is the main site of complement biosynthesis, artificially low plasma levels of C3 and C4 might exist in the first one-two weeks after transplantation, and this could minimize the usefulness of C3a/C4a levels as an indicator of pathologic events until liver function is restored. Therefore, levels of C3a/C4a immediately after transplantation, which were shown to be elevated, may actually underestimate the extent of complement activation. Consequently, in some instances, it may be preferable also to obtain plasma C3/C4 levels as well as the C3a/C4a measurements so that the full extent of activation can be assessed. Therefore, longitudinal measurement of complement factors C3a and C4a provide an additional valuable tool in the assessment of liver and other organ transplant patients.

It is shown in the Examples below that the lectin pathway plays an important role in complement activation in liver transplant patients. Unique patterns of C3a and C4a levels, together with organ-specific parameters, correlate with a number of pathological conditions and clinical events. Studies involving discrete patient subpopulations (e.g. hepatitis or CMV patients) yield information that can be applied in routine monitoring of the organ and immune status of these patients. The results indicate that resolution of acute rejection episodes and viral infections can be effectively monitored by longitudinal measurement of these activation products of complement. The data indicate that characteristic profiles and patterns of C3a/C4a levels can be used as reliable monitors of rejection episodes, immune status and/or viral infections in allograft, and presumably also in xenograft, organ transplant patients.

These results demonstrate that the methods provided herein can be used as diagnostic tools to assess disorders and conditions associated with each of the alternate, classical and lectin pathways. Further, these assays can be used in other methods, such as methods of monitoring therapy, screening for drugs, assessing toxicity and efficacy of treatments.

The following examples are included for illustrative purposes only and are not intended to limit the scope of the invention.

EXAMPLE 1

Materials and Methods
Reagents:

Futhan was obtained from Banyu Pharm. Co., LTD., Tokyo, Japan. The complement C3a (code RPA 518) and C4a (code RPA 519) Biotrak RIA assay kits were obtained from Amersham Life Sciences, Arlington Heights, Ill. EDTA Na$_4$ (sigma grade) was purchased from Sigma, St Louis, Mo. All other chemicals, buffer salts and reagents were analytical reagent grade.

Blood Samples:

Blood samples of 5–10 ml were drawn from normal donors, liver transplant and SLE (lupus) patients under an approved Human Subjects protocol #96-293 and all individuals were asked to sign an informed consent form agreeing to be voluntary donors. Normal donors were a random group of male and female individuals between the ages of 27–48. Liver transplant patients were selected from a group of patients being routinely followed at The Scripps Clinic Foundation by Dr. John Brems. None of these organ transplant patients were experiencing acute rejection episodes at the time that the blood was drawn.

Blood Processing Protocols:

Blood samples were either drawn into EDTA tubes (Venoject, Terumo Corp. Elkston, Md.) or Futhan/EDTA tubes (Venoject, Terumo Europe, Leuven, Belgium). The plasma was collected immediately by centrifugation at 2000 g for 15 min. at 4° C. unless otherwise indicated. The plasma samples were either processed immediately for analysis or snap frozen in liquid nitrogen and stored at −70° C. Frozen samples were thawed at 4° C. and processed as described in the text.

Assay Procedure and Data Analysis:

Equal volumes of the plasma sample and the precipitating reagent supplied in the Biotrak RIA kits were mixed by thorough agitation and incubated at rt. for 5 min. The mixture was then centrifuged at 2500 g for 15 min. at 4° C. The supernatant from each sample tube was collected for analysis in the RIA assay. A 50 µl aliquot of the original or diluted supernatant was mixed with 50 µl of the Biotrak assay buffer in a 12×75 mm polypropylene tube. The I$^{125}$ labeled C3a or C4a and the specific antibody solutions (50 µl each from the kit) were added and incubated at rt. for 30 min. (for antibody to C3a, C4a, C5a and des Arg derivatives thereof, see Hugli et al. (1975) *J. Biol. Chem.* 250:1472–1478; Hugli (1975) *J. Biol. Chem.* 250:8293; and Hugli et al. (1981) *J. Biol. Chem.* 256:2685–2692). A 50 µl aliquot of the second antibody (goat anti-rabbit) was added to the tube and the mixture incubated for an additional 30 min. at rt. Two ml of isotonic saline was added and the tube was centrifuged at 2000 g for 10 min. at 4° C. to pellet the antigen-antibody complexes. The supernatant in the tubes was decanted and the tubes were counted for 1 min. in a Cobra Auto-gamma Model 5002 (Packard Instrument Co., Meriden, Conn.) scintillation counter. Analysis of each sample was performed in duplicate. Data was analyzed using RiaSmart software supplied by Packard Instruments and installed in the Cobra Auto-gamma counter.

Results

Experiment 1

The level of Futhan that was required to protect EDTA plasma samples from in vitro complement activation versus time was examined.

The first experiment (designated experiment 1 herein) showed that Futhan inhibits in vitro complement activation in EDTA (10 mM) plasma. Blood from a normal donor was drawn into EDTA and 0 to 0.2 mg/ml Futhan was added over time indicated. Plasma was recovered within 30 min. of being drawn and a precipitating agent was added to the 0 time plasma sample (EDTA/p10) to prevent further C-activation. An EDTA/Futhan plasma sample (EDTA/p1) and an EDTA/Futhan blood sample (EDTA/b1) were stored for 1 hr. at 22° C. A separate set of EDTA/Futhan plasma samples were either stored at 4° C. for 24 hr (EDTA/p4) or frozen at −70° C. for 24 hr (EDTA/pF) and then thawed for analysis. C3a and C4a levels were determined using a radioimmunoassay procedure.

Samples containing Futhan could be stored for 24 hr either on ice or frozen and thawed and still showed minimal generation of either C3a or C4a. When no Futhan was present, the levels of C3a in EDTA plasma were only slightly elevated compared to samples containing Futhan, even after standing for 24 hr. at 4° C. Fresh EDTA-plasma samples were collected just prior to analysis (EDTA/p0). The whole blood (EDTA/b1) and plasma (EDTA/p1) samples were stored at room temperature for one hour and a separate set of plasma samples were stored for 24 hrs at 4° C. (EDTA/p4) or frozen (EDTA/pF) at −70° C. and thawed prior to analysis. The C3a values for these samples were not significantly different for any of the various handling conditions, and adding Futhan to the EDTA samples had only a minimal effect since there appears to be little C3 activation in normal plasma under these conditions.

When Futhan levels were present at 0.2 mg/ml, the C3a levels in all the samples were actually somewhat higher than at the lower Futhan levels. This activation may be a result of non-specific effects from exposing the plasma to elevated salt concentrations. These same handling and storage conditions did have variable effects on C4 activation in the EDTA plasma (i.e. in the absence of Futhan). The characteristic activation of C4 in normal EDTA plasma was abolished when Futhan was added to these samples. Consequently, the major effect of adding Futhan to normal EDTA plasma was to reduce C4a, but not C3a, generation. Futhan levels as low as 0.01 mg/ml appeared to be effective in protecting normal plasma from C-activation under the conditions described.

These data indicated that activation of complement in EDTA plasma results from either the classical or lectin pathway of activation, since primarily C4a was generated. Furthermore, the enzyme clearly prefers cleaving C4 over C3.

Experiment 2

Commercial blood drawing tubes (EDTA/Futhan Venoject™ tubes, Terumo Co.) containing 5 mg of $Na_2$-EDTA and 0.5 mg Futhan per tube were designed for collecting 2.5–5.0 ml of blood. Although Futhan at the level of 0.01 mg/ml was effective in protecting normal plasma from C4 conversion. Higher concentrations will be required to protect C4 in patient plasma where the conversion of C4 (i.e. the converting enzyme levels) is significantly greater. The precise concentrations can be determined empirically. These vacuum tubes were developed to stabilize complement in blood samples being drawn for either research or clinical applications.

Futhan is an inhibitor that exhibits a broad specificity for many of the blood serine proteinases. General serine proteinase inhibitors of the coagulation system such as benzamidine (an inhibitor of Factor VII, Xa, thrombin, plasmin, and C1s) or Trasylol (an inhibitor of thrombin, kallikrein and plasmin) were compared with Futhan for their effectiveness in controlling C-activation. It is known that certain of the coagulation proteinases can convert C3 and C4 (Pfeiffer et al. (1997) in Techniques in Protein Chemistry VIII Techniques in Protein Chemistry VIII, Marshak, Ed., pp. 363–369, Academic Press, San Diego), and therefore it is important to inhibit the complement and coagulation enzymes in plasma to prevent potential non-complement enzymes from causing C-activation.

In the absence of EDTA, neither benzamidine nor Trasylol, either individually or in combination, could fully stabilize C3 (i.e. prevent alternative pathway C-activation) versus time (FIG. 2). As shown in FIG. 2, complement activation in blood was measured in the presence of several anti-coagulants, with and without EDTA (0.5 mg/ml) added. Whole blood from a normal donor was drawn into 0.15 mM benzamidine, 20 $\mu$M Trasylol or 0.1 mg/ml Futhan and processed either immediately (0 time) or after 60 min. at rt, and then analyzed for C3a and C4a.

Benzamidine and Trasylol failed to prevent C3a generation in these blood samples, while Futhan was effective inhibitor. When these same additives were combined with 10 mM EDTA there was no generation of C3a. Extensive conversion of C4 occurred except when Futhan was present.

It should be noted that in the experiment 1, discussed above, (experiment 1) the level of C3a generated in whole EDTA blood at room temperature after 60 min. was approximately 600 ng/ml, while in FIG. 2 the C3a values were approximately 200 ng/ml using the same conditions. The difference in these two results reflects variations in C-activation. Such differences are commonly observed among individual "normal" donors. The blood donor in experiment 1 was not the same as the donor in FIG. 2. From these data it is clear that neither inhibitor of coagulation proteinases was capable of preventing C3 conversion, but the inhibitors were effective in minimizing C4 conversion in whole blood.

When EDTA was added to the blood there was a remarkable increase in C4 conversion, but virtually no C3 was converted. The enzyme responsible for C4 conversion in the presence of EDTA is shown herein to be MASP-2 of the lectin pathway and not C1s of the classical pathway, because C1 is effectively inactivated by removing calcium ions (Arlaud et al. (1987) *Immunol Today* 8:106–111) and any C1s that would have been activated would be under the rigorous control of C1 INH (Sim et al. (1980) *Biochem Biophys Acta* 612:433–449).

Futhan, with or without EDTA added, was effective in stabilizing C3 and C4 in normal whole blood for up to one hour at room temperature (FIG. 2). When blood samples were drawn and immediately placed on ice, the samples were stabilized for a much longer time. In this experiment, whole EDTA (0.5 mg/ml) blood from a normal donor was incubated at 4° C. with and without 0.1 mg/ml Futhan added. The C3a and C4a levels were determined versus time over 23-hr. C3a levels in EDTA blood were only slightly higher than C3a levels in Futhan/EDTA blood versus time. C4a levels in EDTA blood continued to rise throughout the entire 23-hr period from a level of 300 ng/ml to more than 1700 ng/ml of C4a. When the blood was drawn into Futhan/EDTA, no C4a was generated over the entire 23-hr period.

Note that EDTA was sufficient to prevent C3a generation in normal blood at 4° C. over a 27-hr period, but even at 4° C. significant quantities of C4a can be generated in EDTA blood unless Futhan is added. These results define a suitable window of opportunity for collecting stabilized plasma from blood samples drawn into Futhan/EDTA, and this protocol can be applied to research and clinical samples.

The levels of C3a and C4a in EDTA-blood obtained from normal donors, processed immediately, with and without Futhan present were examined. This data helps to establish a baseline for circulating levels of these factors in normal individuals. The average values for C3a and C4a in EDTA-plasma and in EDTA/Futhan plasma were obtained from a total of 20 individuals. The plasma was recovered immediately from the blood samples and analysis gave the data shown in Table III.

TABLE III

NORMAL PLASMA LEVELS OF C3a AND C4a[*]

| | EDTA | | EDTA/Futhan | |
|---|---|---|---|---|
| | C3a (ng/ml) | C4a (ng/ml) | C3a (ng/ml) | C4a (ng/ml) |
| I | 599 ± 263 (349–1344) | 316 ± 169 (130–774) | 454 ± 182 (213–974) | 192 ± 107 (106–532) |
| II | 484 ± 110 (349–722) | 268 ± 95 (130–433) | 426 ± 144 (213–730) | 174 ± 78 (106–331) |

[*]Values given for n = 20 donors, 11 male, 9 female, ages 26–48. Blood samples were drawn in EDTA (1 mg/ml) or Futhan (0.2 mg/ml) and EDTA. The samples were then processed immediately at room temperature (rt). The standard deviations (±) and range of values (in parentheses) are also reported.
I: reports total data set containing several apparent outlying values; II: reports results when values falling outside of $\chi \pm 2\sigma$ (99%) were eliminated. The t-test indicated that mean values for C3a in EDTA versus Futhan/EDTA plasma were not significantly different. The difference between the C4a values obtained from EDTA and Futhan/EDTA plasma in II was significant (p = 0.002).

This study involved 11 male and 9 female donors between the ages of 27–48. The results show a statistically significant protective effect of the Futhan. Comparison of the values in Table III (i.e. immediate processing to collect plasma) with values obtained from whole EDTA blood held on ice for only a few hours (experiment 2B), it is clear that C4 is not protected even in normal blood without the addition of Futhan.

This data also demonstrates that some donors who present themselves as "normal" can have background levels more than 2 s.d. higher than the average value, as shown in column I of Table III, by the range of values in parenthesis.

The fact that the C4a levels were significantly lower in Futhan/EDTA than in EDTA alone indicates that low levels of in vitro activation commonly occur in "normal" plasma.

Complement activation in EDTA plasma was compared with activation in EDTA/Futhan plasma at room temperature (22–24° C.) over a period of one hour (experiment 3A). C3a and C4a generation in EDTA plasma from "normal" donors (average values, n=11) was effectively inhibited by Futhan. All blood samples were drawn into EDTA, with and without 0.1 mg/ml Futhan present, and the plasma was collected (see Materials and Methods) and frozen at −70° C. These samples were thawed at 4° C. and analyzed after 0 and 60 min. at rt. The control C3a levels were virtually unchanged versus time with or without Futhan added. C4a levels in the control EDTA plasma rose from 242+/−95 ng/ml to 768+/−392 ng/ml over 60 min. The C4a levels in Futhan/EDTA plasma at 0 time were lower than in EDTA alone and remained unchanged after 60 min. at rt.

The data was reported as average levels (n=11) and the only value that changed during this period of time was the C4a level. C4a was elevated approximately 3–4 fold on average over 60 min. in EDTA plasma for this group of 11 normal blood donors. It should be pointed out that C4a generation does vary significantly between "normal" individuals, and C4a levels in normal EDTA plasma usually rose significantly versus time even at 4° C. A dramatically different pattern of C4 activation was observed in the plasmas of liver transplant patients compared with "normal" individuals [experiment 3B]. C3a and C4a generation was examined in EDTA plasma of liver transplant patients (average values, n=19) with and without 0.1 ng/ml Futhan present. These subjects were stable transplant patients not undergoing a clinically detectable rejection episode. The background plasma C3a and C4a levels at 0 time were significantly higher than were determined in plasma from the "normal" population. After 60 min. at room temperature the average C4a level in the patient EDTA plasma had risen to be 25–50 times higher than in normal EDTA plasma.

All samples were analyzed at 0 time and after 60 min. at room temperature. The patient C3a and C4a levels were markedly higher than for the normal donors at time points. The average patient C4a level in EDTA plasma at 0 time was 4020+/−6100 ng/ml indicating a wide variation in the in vitro activation. The C4a level in Futhan/EDTA was 826+/−419 ng/ml indicating that during processing there is still extensive C-activation in the patient's blood compared with normal individuals. C3a and C4a levels in EDTA plasma were greatly elevated after 60 min. and Futhan effectively prevented this time-dependent activation.

Activation of C4 in a lupus (SLE) patient was examined. The level of C3a and C4a in EDTA/Futhan plasma was much higher than in normal EDTA/Futhan plasma (experiment 4). The level of C4a in EDTA plasma from the lupus patient exceeded 10 μg/ml after 60 min. at 37° C. compared with 8–9 μg C4a/ml in normal plasma from two subjects. Although the rate of C4 activation in the SLE patient's EDTA plasma at 37° C. was very high, this appears to be a relatively normal in vitro activation level for this temperature. These 37° C. results illustrate that without chilling blood immediately once it is drawn, and/or adding Futhan to the samples, background levels of C4a will rapidly rise.

Discussion

A kinetic analysis of C4 conversion in blood held at 4° C. versus time demonstrated the overall effectiveness of Futhan/EDTA as a stabilizer. Since neither C3a nor C4a levels rose over a period of 27 hr at 4° C. when Futhan/EDTA was present, blood samples can be collected in Futhan/EDTA, chilled and analyzed hours later or shipped for analysis at another site, and thus, can serve as indicators of C activation in vivo.

As can be seen in Table III, the baseline values for C3a and C4a remain low even in EDTA alone when the plasma was recovered from the blood and processed immediately. The addition of Futhan to these samples caused only marginal reduction in the C4a levels and no significant reduction in the C3a levels. These data matched published data for best estimates of the minimal background or baseline circulating levels of C3a or C4a in a normal population (Watkins et al. (1989) *Lancet* 1:896–897).

In experiment 4, the C4a values in EDTA plasma were the only ones to rise versus time and these levels remained quite low compared to those of liver transplant patients. The C4 conversion values in this group of patients were remarkably high (20-fold times the normal group) even at 0 time (i.e. the actual time it takes to spin down the blood and recover the plasma and add precipitating agent to stop the activation). After 60 min. the conversion of C3 and C4 were extensive in the patient EDTA plasma. This data indicates that, although the proteinase prefers C4 over C3, at high levels the enzyme is capable of cleaving C3 and C4.

These results demonstrate that Futhan remains protective even when the proteinase level is markedly higher than in normal plasma, thereby demonstrating that the C3a/C4a assay system has clinical application.

EXAMPLE 2

Plasma C3a and C4a Levels in Liver Transplant Recipients

A study was designed to obtain longitudinal complement activation data from an assortment of liver transplant patients. The goal was to monitor ongoing immune events by analyzing the circulating levels of C3a and C4a over a period of more than a year in order to correlate C3a/C4a levels with known pathological conditions of these patients. These experiments show that MASP activity can be used to assess patient status in an exemplary condition.

Acute rejection gave a characteristic increase in C3a, C4a and γ-GT levels, which resolved after high dose steroid treatment. CMV and hepatitis C infections and hepatitis B infection were detected by biopsy and correlated with marked and prolonged elevations in C4a levels, but not C3a levels.

Also observed was very high in vitro (also referred to as ex vivo) activation of complement in EDTA plasma from all transplant patients compared to non-transplant normal individuals. As shown in Example 1, this activity results from MASP activity, since no proteases of the coagulation or other complement activation pathways could be demonstrated in EDTA plasma (see, FIG. 2). The C4 converting activity in EDTA plasma is fully inhibitable by Futhan. Consequently, circulating levels of the complement breakdown products, i.e., the anaphylatoxins, can be monitored in blood drawn into Futhan/EDTA, and the levels of MASP enzyme can be estimated in EDTA plasma.

The results in this example, show that the MASP enzyme is responsible for complement activation in the liver transplant patients during viral infection, thereby demonstrating that MASP activity can be used as a indicator of certain diseases or disorders, particularly any that involve exposure of neutral sugars, such as viral and parasitic infection and tissue injury, particularly immune injury.

The results of this study also demonstrate that MASP is activated n vivo by viruses. The profile of the activation of C3 and C4 correlates with viral infection, such as hepatitis C and CMV as confirmed by tissue biopsy in these patients. Also, tissue injury leading to exposure of neutral sugars on the cell surface can activate MASP enzyme. Mechanism for MASP activation in tissue injury.

MASP is activated by neutral sugars, such as mannose, or any event that exposes neutral sugars. The MASP enzyme is activated in the complex, but not active in fluid phase on the substrate C3 and C4, until dissociated, such as by metal chelation in vitro. In vivo it appears that the MASP enzyme acts locally in the complex by achieving high effecting concentrations at the site of action, such as on a viral particle or injured cell surface.

Study

Liver transplant patients were enrolled in a long-term prospective study designed to investigate correlations between plasma complement C3a or C4a levels and various postoperative complications. Longitudinal EDTA-plasma levels of C3a and C4a were measured by quantitative radioimmunoassay. Acute rejection gave a characteristic and marked increase in blood C3a, C4a and gamma-glutamyl transferase (γGT) levels, which rapidly resolved after high dose steroid treatment.

Cytomegalovirus (CMV) infections in two of three patients gave an initial small increase only in C3a levels (i.e. alternative pathway activation), followed approximately six weeks later by a marked increase in C4a levels (i.e. classical or lectin pathway activation) with a smaller but corresponding elevation in C3a levels. In a third patient diagnosed for CMV infection the complement activation profile was complicated by a coincident minor rejection episode, however a late stage elevation in C4a was also noted. Two patients experiencing biopsy proven recurrent hepatitis C infections following transplantation exhibited increases in γGT and C4a levels, without a significant increase in the level of C3a. Several hepatitis C and one hepatitis B patient had multiple activation episodes involving marked elevation in both C3a and C4a without detectable increases in the enzymes conventionally used to monitor liver function. The results presented herein show that in vitro activation of complement in EDTA plasma from all transplant patients was abnormally high.

Since the release of MASP from the complex in vitro is shown herein to be responsible for in vitro complement activation in these patients' plasma, sub-clinical rejection episodes, tissue injury, or viral infections may be effectively detected or monitored by measuring the ability of plasma samples from liver transplant patients to generate excessive quantities of C3a/C4a in vitro.

Routine measurement of plasma complement products using the methods herein should provide an early non-invasive mode for detection of viral infections and serve to monitor other changes in the status of a patient's immune system.

Materials and Methods

Blood and urine samples were collected over a period of two years from 63 liver transplant patients during routine post-operative clinical visits. The patients' identities were concealed and no selection process or attempt was made to recruit patients for any other reason than that they had undergone orthotopic liver transplantation at The Scripps Clinic and Research Foundation. Immunosuppression was initiated with a regimen of cyclosporine A (CsA), azathioprine and steroids. Treatment for some of these patients was switched to FK506, but none was treated with OKT3.

Patients were seen weekly in the outpatient transplant clinic after transplantation until their liver function tests stabilized. After that time, patients were seen at various intervals, depending on their clinical course. Measurement of the relevant clinical parameters was obtained during each visit. Liver biopsies were obtained whenever there was an abnormality in liver function tests.

Blood and urine samples were obtained for complement studies during each outpatient visit. These samples were collected in tubes containing EDTA and immediately placed on ice, except for the EDTA plasma samples used in the in vitro activation studies. These were kept at room temperature. The plasma was recovered from the blood samples by sedimentation at 1500×g and plasma and urine samples were stored at −20° C. until they were analyzed. The samples were thawed and analyzed batchwise using commercial human C3a and C4a Biotrak kits (Amersham Life Sciences Inc., Arlington Heights, Ill.).

Correlations were made between the patient's clinical course and C3a/C4a patterns in the blood and urine samples. Retrospective analysis of the data was then performed comparing the patient's clinical course with major changes observed in C3a/C4a levels.

Results

More than 400 samples were obtained from 63 transplant patients after consent was obtained from each to enter the study. Ten of these patients provided between 7 and 20 plasma samples each over a period of 2 to 109 weeks after organ transplantation. These ten cases gave serial profiles that characterized the usual pattern of post-transplant recovery. Many of the other patients failed to provide adequate numbers of samples to develop longitudinal profiles suitable for interpretation or correlation with the clinical data. Patients were initially grouped according to their primary disease (i.e., hepatitis C, sclerosing cholangitis, biliary cirrhosis and alcohol cirrhosis). Urine samples were initially examined in parallel with the plasma samples, but these values proved to be uninformative (i.e., generally low levels of C3a and C4a were obtained) and so urine collection was eventually discontinued.

The ten patients whose longitudinal data are reported in this study developed various complications that resulted in marked transient complement activation patterns.

In experiment 1, it was found that the average C3a and C4a levels for all 144 samples obtained from these ten patients were significantly elevated compared with plasma levels in normal non-transplant individuals. Average C3a and C4a levels in EDTA plasma were determined 11 normal individuals and compared to all samples provided by the 11 patients in this study (n=144: average level and s.e.m.). The significantly higher average C3a and C4a levels in the organ transplant patients reflect generally elevated baseline values as well as marked elevation during the pathological episodes that occurred in these patients. In fact, the average C3a and C4a levels in plasma samples from all 63 patients were markedly elevated compared with levels in non-transplant "normal" individuals.

A well-characterized complication in organ transplant patients is acute rejection. Acute rejection shows a distinct pattern of complement activation.

Patient 1

One example of an acute rejection episode was observed in one patient, patient 1. In this experiment, serial EDTA-plasma measurements for C3a and C4a levels, bilirubin and γGT levels were determined. This patient developed an acute rejection episode at week 7 causing a large increase in C3a, C4a and γGT levels, whereas bilirubin, SGOT and SGPT levels were only moderately increased. The rejection episode resolved rapidly upon treatment with two 1 g (I.V.) doses of methylprednisolone. The profiles of late phase episodes are illustrated by a C4a>C3a response between weeks 40–60 and another C3a/C4a response at week 78. Although unconfirmed by biopsy, these responses are similar to the profiles observed during hepatitis C re-infection.

This patient (female, 46 years old) had initially been transplanted for primary biliary cirrhosis. At the time of the acute rejection episode (week 7 post-transplant), there was a characteristically abrupt increase in γGT levels, and SGPT (up to 140 I.U.) and SGOT (up to 149 I.U.) were also significantly elevated. Bilirubin remained at approximately the same level throughout (≦2.1 mg/dl). Note that C4a levels rose in parallel with the rise in enzyme markers and attained extremely high plasma levels. The rise in C3a level was less remarkable suggesting classical or lectin pathway activation. The patient was treated intravenously with two 1 g doses of methylprednisolone, after which there was an equally abrupt resolution of the crisis based on normalization of the transaminase profiles. The fall in C4a level parallels that of the transaminases. The acute rejection profile essentially represents a positive control for the C3a/C4a detection system, elevation in clinical parameters such as transaminase levels and bilirubin responses during rejection are well established. Later episodes at 40–80 weeks showed a marked elevation in C3a and C4a levels with only minor changes in the liver function parameters. These later episodes were neither diagnosed nor correlated with detectable clinical events since no biopsy was performed, but may represent either viral infections or some other form of the humoral immune response.

C3a, C4a, γGT and bilirubin profiles were determined for three patients who were diagnosed with CMV.

Patient 2

Patient 2 (female, 67 years old) had initially been transplanted for primary biliary cirrhosis. When she was re-admitted to the hospital at week 5 with CMV infection, as later diagnosed by blood and urine cultures, her liver function appeared normal (Bilirubin 0.9 mg/dl, SGOT 8 I.U., SGPT 12 I.U.). There was a small but distinct peak of C3a at week 5 (perhaps the initial viremia) and then a very large C4a response at week 11 with a much smaller rise in C3a. Clinical liver function parameters for patient 2 were uneventful throughout the 80-week course of monitoring. The patient was diagnosed with CMV at week 5 and during this initial infection episode only C3a levels were elevated. second episode of complement activation occurred at week 11 and this event involved primarily C4 conversion. The cause for this C4a generation was speculated to be a humoral immune response to CMV and this response resolved within two weeks.

This distinct C4a peak results from either immune complex activation of the classical pathway or activation of the lectin pathway associated with viral tissue injury (Epstein et al. (1996) *Curr. Opin. Immunol.* 8:29–35). There were minor pathological signs of liver malfunction at week 11 (SGOT 19 I.U., SGPT 16 I.U.) and the patient complained of flu-like symptoms. CMV infection appeared to cause remarkable changes in complement activation, whereas the liver function parameters showed only minor fluctuations. The plasma C3a/C4a profile for this patient provides an example of changes in complement activation occurring independent of alterations in conventional enzyme signals. Three weeks later all values, including the complement product levels, returned to normal.

Patient 3

Patient 3 (female, 45 years old) had initially been transplanted for primary sclerosing cholangitis. Cytomegalovirus infection was diagnosed eight weeks post-transplant by percutaneous liver biopsy. A significant elevation in C3a levels was detected at week ten. C4a levels were not significantly elevated at that time. There were no plasma samples obtained between weeks 4–10 when the C3a/C4a levels may have actually peaked. SGOT and SGPT were also slightly elevated at week 10 in this patient (24 and 32 I.U., respectively), but neither γGT nor bilirubin were elevated.

Six weeks after detection of CMV infection (i.e. week 14) there was a marked increase in complement activation factors similar to the pattern observed with patient 2. At this time, C3a and C4a were significantly elevated, but no correlation was made with any detected pathological event and the liver functions (i.e. enzyme levels) now appeared normal. Two later episodes were detected where C3a at 50 weeks and C3a/C4a levels at 84 weeks were markedly elevated. No indication of a clinical episode or elevation in enzymes that monitor liver function were evident during these periods of extensive complement activation.

Clinical liver function parameters for patient 3 were also virtually silent except for a slight rise in SGOT and SGPT at week 8, when CMV infection was first diagnosed. There was elevation only in C3a levels at week 8 followed by elevation in C3a and C4a levels at week 14. Like patient 2, there appears to be a delayed immune response (i.e. at week 14) after the initial CMV infection and this response appears to involve activation of the classical and/or lectin pathway. There is evidence of two additional events for which there is no clinical explanation at this time. One episode occurred between weeks 40 and 60, and involved the alternative pathway of activation (perhaps a minor bacterial infection), and the second episode is evident at week 84 involving primarily the classical or lectin pathway.

Patient 4

Patient 4 (male, 60 years old) had initially been transplanted for chronic active hepatitis C. The complement and enzyme profiles were more complex for this patient because of several known complications. At week 6, 2.2 mg/dl), SGOT (59 I.U.) and SGPT (113 I.U.) were elevated. At week 7, the patient's urine tested positive for cytomegalovirus, but no plasma sample was available for complement measurement until week 13. At week 13 a mild rejection episode was diagnosed by liver biopsy and C4a and γGT levels were elevated, along with other parameters of liver function (SGOT 89 I.U., SGPT 130 I.U.). This episode resolved upon treatment with steroid treatment (2×1 g methylprednisolone i.v.) so that by weeks 16–18 enzyme levels had normalized. Week 21 showed a markedly elevated C4a level while other liver function parameters normalized to near baseline values (Bilirubin 1.7 mg/dl, SGOT 38 I.U. SGPT 53 I.U.). No biopsy was performed or corresponding clinical event was detected but the profile of elevated C4a levels over weeks 20–34 suggests either a late phase response following CMV infection as seen for patients 2 and 3 or represents the response to hepatitis C re-infection of the donor organ.

Thus, clinical liver function parameters for patient 4 indicated two events occurring in the first 20 weeks post-op. At week 11 the patient's urine tested positive for CMV and at week 13 a mild rejection episode was diagnosed through biopsy and the patient was treated with two 1 g (I.V.) doses of methylprednisolone. No complement values were available between weeks 7 and 13, but C4a was elevated at weeks 7 and 13 suggesting a protracted activation episode. There is a second strong C4a signal at week 21 (E) suggesting that between weeks 20 and 30 extensive activation was ongoing. This episode may reflect the delayed humoral immune response to the CMV infection.

Additional Patients

Additional patients suspected of having recurrent viral infections were studied. Four of these patients had initially been transplanted for liver damage caused by hepatitis C and one for Laennec's disease. In all cases, C4a levels rose modestly following diagnosis of the initial viral infection and then a more dramatic second activation event occurred, although the period between the initial infection and this later C4a response varied significantly.

Patient 5

Patient 5 (male, 48 years old) was a hepatitis C patient retransplanted four days after the initial transplant failed from to primary nonfunction. He was treated with intravenous methylprednisolone during weeks 2, 9 and 13 for biopsy-proven rejection episodes, but was only entered in the study 32 weeks post-op. There was a small but significant peak of C4a detected at week 43 and C3a levels appeared to be elevated at week 48, events remain unexplained. A rejection episode was diagnosed through liver biopsy at week 64 with parallel abnormal liver function parameters (γGT 536 I.U., Bilirubin 1.5 mg/dl, SGOT 100 I.U., SGPT 193 I.U.). Plasma samples were not obtained for complement measurements at that time. At week 74, there was a dramatic increase in C4a levels, together with lesser increases in C3a, γGT and SGPT. The patient was suspected of having recurrent hepatitis C infection at this time, and the diagnosis was confirmed by liver biopsy. Although an exact time of the primary infection cannot be assigned, the humoral immune response to the viremia may explain elevated C4a levels at week 74. As was observed with CMV infection, hepatitis C infection appears to elicit a late phase complement activation episode without perturbing liver function.

Patient 6

Patient 6 (female, 60 years old) was a hepatitis C patient treated with intravenous methylprednisolone during weeks 12, 15 and 19 for suspected acute cellular rejection which was not confirmed by biopsy. The T-tube was removed during week 15 and coincided with a strong increase in γGT and, to a lesser degree, C4a, SGPT (92 I.U.) and SGOT (370 I.U.). The patient was suspected of having recurrent hepatitis C infection beginning at week 24, at which time C4a and γGT levels began to rise. The recurrent hepatitis was confirmed during week 33 by liver biopsy. C4a, SGOT and SGPT levels were still increasing at week 33 while γGT levels were declining. A feature that may distinguish the enzyme profile in CMV from hepatitis C is that γGT is not elevated with CMV, but it is with hepatitis C. The complement product profiles for both types of viral infections are similar except that the C4a levels appear to remain elevated for a longer period in hepatitis patients.

Patient 7

Patient 7 (male, 48 years old) received a transplant for Laennec's cirrhosis. C3a levels were elevated when the patient entered the study at post-operative week six, but these levels rapidly returned to baseline. A moderate elevation in γGT levels occurred at week 18, but this could not be correlated to any pathological event. The patient was admitted to the hospital at week 42 and liver biopsy revealed an infection with hepatitis C. This episode coincided with dramatic increases in C3a and C4a levels in earlier plasma samples, whereas all other clinical parameters remained unchanged. In this patient the C3a/C4a levels returned to baseline after several weeks, perhaps because the immune response had been effective in removing the virus.

Patient 8

Patient 8 (female, 49 years old) had initially been transplanted for hepatitis C liver damage. A mild rejection episode was diagnosed through liver biopsy at week 6 and treated with two 1 g (I.V.) injections of methylprednisolone. A minimal increase in the C4a level was observed at that time. The T-tube was removed at week 14 coinciding with an increase in C3a levels. Another increase in C3a and γGT levels occurred at week 28 and was perhaps associated with trauma from the surgical repair of a hernia. Significant increases in C3a and C4a levels occurred around week 65 that could not be correlated to any pathological condition. Since this was a hepatitis C patient, the response may be related to a recurrence of hepatitis C re-infection of the donor organ.

Patient 9

Patient 9 (male, 38 years old) was also transplanted for chronic active hepatitis C. This patient recovered very well and gave no pathological indications of infection or liver dysfunction despite two brief spikes in C3a and C4a levels at weeks 42 and 66. All of the liver function parameters for this patient remained normal throughout the whole recovery period. As in patient 8, the complement activation profile indicates that there clearly were significant humoral immune events occurring. However, since no clinical indicators existed, hepatitis C re-infection was not confirmed by biopsy.

Patient 10

Patient 10 (male, 20 years old) was transplanted for fulminant liver failure due to hepatitis B. Immunosuppression involved oral methylprednisolone and CsA which was replaced with FK506 at week 8. The patient was readmitted to the hospital at week 5 for internal bleeding. The C3a and C4a levels were elevated at week 9 but rapidly normalized as the bleeding was controlled. Two episodes occurred showing high levels of C3a and C4a at week 28 and 56, but no clinically diagnosed pathological condition could be correlated to these episodes. This pattern is consistent with hepatitis B re-infection followed by an immune response similar to that observed in the hepatitis C patients.

Other Results

C3a and C4a levels were measured in randomly selected EDTA plasma samples from 19 of the liver transplant patients (patients other than the 10 reported in this study), at 0 time and after 60 min. at room temperature. Note that on average there is extensive in vitro complement activation continuing in the EDTA plasma of the organ transplant patients compared with non-transplant control individuals. This level of in vitro activation of complement was unexpected and it indicates a new parameter, the kinetics of in vitro activation, that should be useful in evaluating the immune response in these patients as well as others.

The levels of C3a/C4a in individual transplant patients were widely variable at 0 time. After 60 minutes at room temperature the in vitro conversion of C4 to C4a and C4b was nearly complete in the plasma from many of the patients but remained little changed in others. The mechanism of this in vitro activation process involves the lectin pathway of complement activation since neither the classical nor alternative pathway remain active in EDTA. This data clearly indicates that marked differences in complement activity do exist between organ transplanted and "normal" non-transplant individuals that may be useful in evaluating organ status.

Discussion

Several previous studies involving immunologic disorders have established a correlation between elevated levels of complement split products and disease activity in systemic lupus erythematosus (SLE) (Buyon et al. (1992) *Arthritis Rheum.* 35:1028–1037), acute rejection in renal allograft recipients (Bechtel et al. (1994) *Transplantation* 58:905–911; Feucht et al. (1993) *Kidney Int.* 43:1333–1338), and post-reperfusion syndrome in liver transplantation (Ronholm et al. (1994) *Transplantation* 57:1594–1597). Transplanted organs in general may be prone to classical pathway activation through low levels of anti-graft antibodies deposited continuously on the vascular endothelium of the allograft. Whereas C3a/C4a diffuse away from the site of generation and are cleared through the kidneys (Abou-Ragheb et al. (1991) *J. Clin. Lab. Immunol.* 35:113–119), some of the C3b/C4b remains bound to the activating surface/antibody complex and may contribute to an inflammatory or immunologic response by binding to the complement receptors on neutrophils and B lymphocytes (Baldwin et al. (1995) *Transplantation* 59:797–808; Boettger et al. (1987) *Immunology Today* 8:261–264; Ochs et al. (1983) *Clin. Exp. Immunol.* 53:208–216; Berger (1998) Complement-mediated phagocytosis. The human complement system in health and disease.; Volanakis et al. eds., New York: Marcel Dekker, Inc., 12, p. 285–308; Wahlin et al. (1983) *J. Immunol.* 130:2831–2836).

Cleavage of C3 appears to occur less often than C4, except for surgical tissue injury and/or bacterial infections. Since C3b has a higher affinity for CR1 than C4b, inflammatory and immunomodulatory effects may be more pronounced when C3 is converted. Since C3a and C5a anaphylatoxins are strong proinflammatory mediators (Hugli (1990) *Curr. Top. Microbiol. Immunol.* 153:181–208; Hugli (1984) Structure and Function of the Anaphylatoxins.; Springer-Verlag, Heidelberg: Springer-Verlag, 7, p. 193–219; Meuer et al. (1981) *Inflammation* 5:263–273) they may enhance pathological conditions associated with acute organ rejection. Complement activation is controlled by powerful regulatory factors, in plasma and on cells, and should these mechanisms be altered or circumvented allowing terminal complement components (i.e. C5b-9) to be recruited, then they too may cause serious damage to the grafted organ (Brauer et al. (1995) *Transplantation* 59:288–293).

The data presented in this example indicates that many of the common complications following liver transplantation result in different but characteristic patterns of complement activation. In particular, as shown herein, acute rejection episodes are associated more with increased levels of C4a, and less with significant elevation of C3a, coupled with marked changes in liver function parameters. Classical pathway activation of complement concurrent with acute immune liver damage is believed to be a typical form of complement involvement. Increased C4a levels were also associated with an apparent secondary immune response (i.e. 6–12 weeks) following primary CMV infection. There were no overt clinical signs of altered liver function in these patients. Limited classical pathway activation should result from generation of viral/antiviral immune complexes produced by the humoral immune response to these infecting agents. The responses observed in this study correspond to results obtained from renal transplant patients where the time between the first episode of symptomatic CMV and detection of IgG antibodies was 9–38 weeks (Manez et al. (1995) *Transplantation* 59:1220–1223).

These studies indicate that where liver function tests fail to indicate the extent of the viremia, then C4a levels should be a useful signal and/or monitor for the course of the viral infection. Recurrent hepatitis C infections show C4a profiles generally similar to those during CMV infection, but in this case liver function parameters were also often elevated, perhaps indicating greater tissue injury. The activation mechanism for persistent C4 conversion following hepatitis infection may again involve immune complexes formed between the viral particles and the antibody. Persistence of elevated C4a levels may be an indication of chronicity of the hepatitis infection. It appears from the data that MASP-2 (Thiel et al. (1997) *Nature* 386:506–510) of the lectin pathway may play a major role in the activation of complement during these episodes.

There was generally less elevation in C3a than in C4a levels during these monitored events. Samples available from patients with acute CMV infection showed elevation of C3a levels, but not C4a levels, during the very early phase, indicating an initial alternative pathway activation followed by classical and/or lectin involvement. This pattern should be diagnostically useful.

Two patients with renal problems not included in this study showed extremely high plasma C3a and C4a levels, presumably as a result of reduced renal filtration rates. The C3a levels in patients experiencing either a rejection episode or recurrent hepatitis C infections were not uniformly elevated, consequently C3a levels appear decidedly less valuable than C4a levels as a monitoring tool or as a diagnostic marker of organ status, particularly in liver transplants.

This study shows how valuable longitudinal data for the complement split products is in evaluating the various complications often associated with organ transplantation. It also shows the need to gather multiple samples versus time in order to detect transient or progressive changes indicative of pathological disorders. The C4a profiles that exist independent of alterations in liver functional responses appear to be of most interest.

Since modifications will be apparent to those of skill in this art, it is intended that this invention be limited only by the scope of the appended claims.

What is claimed is:

1. A method of measuring in vivo complement activation of the lectin pathway in a mammal, comprising:
   obtaining a sample of plasma from the mammal, wherein the plasma comprises a metal ion chelator or an agent that removes or binds calcium ions;
   measuring the kinetics of in vitro complement activation as a function of time or the amount of in vitro complement activation at a preselected time after obtaining the sample; and
   correlating the increase in or amount of in vitro complement activation with the level of in vivo activation of the lectin pathway.

2. The method of claim 1, wherein the complement activation is measured by measuring the change in C4a levels as a function of time.

3. The method of claim 2, wherein C4a levels are measured at a selected time during the linear increase in C4a levels compared to a control at time zero or compared to the level when C4a reaches a maximum.

4. The method of claim 1, wherein levels of activated mannan-binding protein-associated serine protease (MASP) are determined.

5. The method of claim 1, wherein levels of activated MASP-2 is determined.

6. The method of claim 1, wherein levels of activated MASP-2 and MASP-1 are determined.

7. The method of claim 1, wherein levels of activated MASP-2 or MASP-1 are determined.

8. The method of claim 4, wherein the amount or rate is compared to a control.

9. The method of claim 8, wherein the control is a sample from a mammal not afflicted with the condition, or is a sample from the same mammal in the same manner, except that a serine protease is added.

10. The method of claim 1, wherein the mammal is a human.

11. The method of claim 1, wherein the mammal is a non-human.

12. The method of claim 1, wherein the metal chelator is a divalent metal ion chelator.

13. The method of claim 1, wherein the metal chelator is a polycarboxylic acid chelating agent or citrate.

14. The method of claim 1, wherein the metal chelator is ethylenediaminetetraacetic acid (EDTA).

15. A method of detecting or monitoring a condition in a mammal in which complement activation is effected by exposure to neutral sugars, comprising:
    obtaining a sample of plasma from the mammal, wherein the plasma comprises a metal ion chelator;
    measuring the level of in vitro complement activation or the rate of increase thereof,
    wherein the amount of activation or rate of increase reflects the severity or progression of the condition.

16. The method of claim 15, wherein the amount or rate is compared to the amount or rate in a control sample from a mammal not afflicted with the condition or is compared to a control processed in the same manner, except that a serine protease is added.

17. The method of claim 15, wherein the condition is a parasitic or viral infection, organ transplant rejection, inflammatory response, autoimmune disease, or tissue injury.

18. The method of claim 15, wherein the condition that is detected or monitored is acute organ transplant rejection, chronic rejection or incipient rejection.

19. The method of claim 17, wherein the autoimmune disease is selected from rheumatoid arthritis, system lupus erythematosus (SLE).

20. The method of claim 15, wherein the metal chelator is a divalent metal ion chelator.

21. The method of claim 15, wherein the metal chelator is a polycarboxylic acid chelating agent or citrate.

22. The method of claim 15, wherein the metal chelator is ethylenediaminetetraacetic acid (EDTA).

23. A method for accurately determining the in vivo activation of the classical or alternative complement pathway, comprising:
   obtaining plasma from a mammal;
   adding an inhibitor that specifically inhibits mannan-binding protein-associated serine protease (MASP) activity; and
   measuring the level of products of activation of the classical or alternative pathway.

24. The method of claim 23, wherein a metal chelator is added to the plasma.

25. The method of claim 13, wherein one or more of C3a, C4a and C5a are measured.

26. The method of claim 25, wherein the products are detected by enzyme linked immunoadsorbent assays (ELISAs).

27. The method of claim 23, wherein the inhibitor is 6-amidino-2-naphthyl p-guanidinobenzoate dimethanesulfonate.

28. The method of claim 23, wherein MASP is MASP-2.

29. The method of claim 23, wherein MASP is MASP-1.

30. The method of claim 23, wherein MASP is MASP-2 and MASP-1.

31. The method of claim 25, wherein the level of C4a is measured.

32. The method of claim 24, wherein the metal chelator is a divalent metal ion chelator.

33. The method of claim 24, wherein the metal chelator is a polycarboxylic acid chelating agent or citrate.

34. The method of claim 24, wherein the metal chelator is ethylenediaminetetraacetic acid (EDTA).

35. A method of assessing the efficacy of therapeutic treatments, comprising:
   obtaining a first sample of plasma from a subject prior to commencing treatment or after commencing treatment, wherein the sample of plasma comprises a metal chelator;
   determining mannan-binding protein-associated serine protease (MASP) activity in the first sample;
   obtaining a second sample of plasma from the subject after commencing treatment and at a time subsequent to the first sample, wherein the plasma comprises a metal chelator;
   determining MASP activity in the second sample, and comparing the activity of MASP in the samples, wherein a reduction in MASP activity reflects the efficacy of the selected treatment.

36. The method of claim 35, wherein the treatment of a treatment for infectious agents, organ transplant rejection, tissue injury, autoimmune diseases and inflammatory responses in which complement activation is mediated or initiated by exposure of neutral sugars.

37. The method of claim 35, wherein the metal chelator is a divalent metal ion chelator.

38. The method of claim 35, wherein the metal chelator is a polycarboxylic acid chelating agent or citrate.

39. The method of claim 34, wherein the metal chelator is ethylenediaminetetraacetic acid (EDTA).

40. A method of assessing the toxicity or injury of therapeutic treatments, comprising:
   obtaining a first sample of plasma or serum from a subject prior to commencing treatment or after commencing treatment, wherein the plasma comprises a metal chelator;
   determining mannan-binding protein-associated serine protease (MASP) activity in the first sample;
   obtaining a second sample of plasma or serum from the subject after commencing treatment and at a time subsequent to the first sample, wherein the sample comprises a metal chelator;
   determining MASP activity in the second sample; and
   comparing the activity of MASP in the samples, wherein an increase in MASP activity reflects the toxicity of the treatment or injury from the treatment.

41. The method of claim 40, wherein the first and second samples are plasma.

42. The method of claim 41, wherein first and second samples comprise a metal ion chelator.

43. The method of claim 42, wherein the metal ion chelator is a divalent metal ion chelator.

44. The method of claim 42, wherein the metal ion chelator is a polycarboxylic acid chelating agent or citrate.

45. The method of claim 42, wherein the metal ion chelator is ethylenediaminetetraacetic acid (EDTA).

46. The method of claim 42, wherein each sample is a serum sample.

47. A method of screening test compounds as therapeutic agents, comprising:
   obtaining a first sample of plasma from a test animal model for a selected condition or disorder prior to administering the test compound, wherein the sample comprises a metal chelator;
   determining mannan-binding protein-associated serine protease (MASP) activity in the first sample;
   administering the test compounds;
   obtaining a second sample of plasma, wherein the sample comprises a metal chelator;
   determining MASP activity in the second sample, and comparing the activity of MASP in the samples, wherein a decrease in MASP activity is indicative of activity of the test compound for the selected condition or disorder.

48. The method of claim 47, wherein the disorder or condition is viral disease, parasitic infection, tissue injury, organ transplant rejection, autoimmune disease or an inflammatory response.

49. The method of claim 47, wherein the metal chelator is a divalent metal ion chelator.

50. The method of claim 47, wherein the metal chelator is a polycarboxylic acid chelating agent or citrate.

51. The method of claim 47, wherein the metal chelator is ethylenediaminetetraacetic acid (EDTA).

52. A method of assessing the efficacy of therapeutic treatments, comprising:
   obtaining a first sample of plasma from a subject prior to commencing treatment or after commencing treatment, wherein the sample of plasma comprises an inhibitor that specifically inhibits mannan-binding protein-associated serine protease (MASP) activity;
   determining the levels of C3a and/or C4a in the first sample;
   obtaining a second sample of plasma from the subject after commencing treatment and at a time subsequent to the first sample, wherein the plasma comprises an inhibitor that specifically inhibits mannan-binding protein-associated serine protease (MASP) activity;
   determining the levels of C3a and/or C4a in the second sample; wherein a reduction in levels of C3a and/or C4a reflects the efficacy of the selected treatment.

53. A method of assessing the toxicity of or injury from therapeutic treatments, comprising:

obtaining a first sample of plasma from a subject prior to commencing treatment or after commencing treatment, wherein the sample of plasma an inhibitor that specifically inhibits mannan-binding protein-associated serine protease (MASP) activity;

determining the levels of C3a and/or C4a in the first sample;

obtaining a second sample of plasma from the subject after commencing treatment and at a time subsequent to the first sample, wherein the plasma comprises an inhibitor that specifically inhibits mannan-binding protein-associated serine protease (MASP) activity;

determining the levels of C3a and/or C4a in the second sample; wherein a increase in levels of C3a and/or C4a reflects the toxicity of or injury from the selected treatment.

54. A method of screening test compounds as agents for treatments of diseases, comprising:

obtaining a first sample of plasma from a subject prior to commencing treatment or after commencing treatment, wherein the sample of plasma comprises an inhibitor that specifically inhibits mannan-binding protein-associated serine protease (MASP) activity;

determining the levels of C3a and/or C4a in the first sample;

obtaining a second sample of plasma from the subject after commencing treatment and at a time subsequent to the first sample, wherein the plasma comprises a metal chelator and an inhibitor that specifically inhibits mannan-binding protein-associated serine protease (MASP) activity;

determining the levels of C3a and/or C4a in the second sample; wherein a reduction in levels of C3a and/or C4a is indicative of activity of the test compound for the selected condition or disorder.

* * * * *

UNITED STATES PATENT AND TRADEMARK OFFICE
CERTIFICATE OF CORRECTION

PATENT NO. : 6,297,024 B1
DATED : January 16, 2002
INVENTOR(S) : Hugli

It is certified that error appears in the above-identified patent and that said Letters Patent is hereby corrected as shown below:

Column 32,
Line 16, please insert -- C4a, bilirubin( -- between "week 6," and "2.2 mg/dl)"

Column 37,
Line 60, claim 39 should read as follows:
39. The method of claim 35, wherein the metal chelator is ethylenediaminetetraacetic acid (EDTA).

Column 38,
Line 21, claim 46 should read as follows:
46. The method of claim 40, wherein each sample is a serum sample.

Signed and Sealed this

Twentieth Day of August, 2002

Attest:

*Attesting Officer*

JAMES E. ROGAN
*Director of the United States Patent and Trademark Office*